US012570709B2

(12) United States Patent
Yuan et al.

(10) Patent No.: US 12,570,709 B2
(45) Date of Patent: Mar. 10, 2026

(54) SELF-ASSEMBLING PEPTIDE AMPHIPHILES DISPLAYING A TRANSFORMING GROWTH FACTOR BETA 1 (TGF-ß1) MIMETIC EPITOPE

(71) Applicant: Northwestern University, Evanston, IL (US)

(72) Inventors: Shelby Chi Yuan, Evanston, IL (US); Samuel I. Stupp, Evanston, IL (US); Nicholas A. Sather, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 18/578,613

(22) PCT Filed: Jul. 28, 2022

(86) PCT No.: PCT/US2022/074263
§ 371 (c)(1),
(2) Date: Jan. 11, 2024

(87) PCT Pub. No.: WO2023/010082
PCT Pub. Date: Feb. 2, 2023

(65) Prior Publication Data
US 2024/0336666 A1      Oct. 10, 2024

Related U.S. Application Data

(60) Provisional application No. 63/227,097, filed on Jul. 29, 2021.

(51) Int. Cl.
*C07K 14/495* (2006.01)
*A61K 9/51* (2006.01)
*A61K 38/00* (2006.01)
*A61P 21/00* (2006.01)

(52) U.S. Cl.
CPC .......... *C07K 14/495* (2013.01); *A61K 9/5161* (2013.01); *A61P 21/00* (2018.01); *A61K 38/00* (2013.01)

(58) Field of Classification Search
CPC ..... C07K 14/495; A61P 21/00; A61K 9/5161; A61K 38/00
See application file for complete search history.

(56) References Cited

U.S. PATENT DOCUMENTS

| | | | |
|---|---|---|---|
| 5,661,127 A | 8/1997 | Bhatnagar et al. | |
| 5,780,436 A | 7/1998 | Bhatnagar et al. | |
| 7,030,167 B2 | 4/2006 | Gunther | |
| 7,371,719 B2 | 5/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,076,295 B2 | 12/2011 | Hulvat et al. | |
| 8,080,262 B2 | 12/2011 | Lee et al. | |
| 8,114,834 B2 | 2/2012 | Hsu et al. | |
| 8,114,835 B2 | 2/2012 | Mata et al. | |
| 8,124,583 B2 | 2/2012 | Stupp et al. | |
| 8,138,140 B2 | 3/2012 | Stupp et al. | |
| 8,236,800 B2 | 8/2012 | Degrado et al. | |
| 8,450,271 B2 | 5/2013 | Shah et al. | |
| 8,512,693 B2 | 8/2013 | Capito et al. | |
| 8,546,338 B2 | 10/2013 | Donners et al. | |
| 8,580,923 B2 | 11/2013 | Stupp et al. | |
| 8,748,569 B2 | 6/2014 | Stupp et al. | |
| 8,772,228 B2 | 7/2014 | Stupp et al. | |
| 9,011,914 B2 | 4/2015 | Po et al. | |
| 9,040,626 B2 | 5/2015 | Chien et al. | |
| 9,044,514 B2 | 6/2015 | Xu et al. | |
| 2009/0269847 A1 | 10/2009 | Stupp et al. | |
| 2010/0266557 A1* | 10/2010 | Shah .................. | A61K 38/1841 514/21.7 |
| 2012/0264912 A1* | 10/2012 | Stupp ..................... | A61P 35/00 530/328 |
| 2012/0294902 A1* | 11/2012 | Stupp ..................... | C07K 2/00 530/300 |

(Continued)

FOREIGN PATENT DOCUMENTS

| | | |
|---|---|---|
| WO | WO 2020/198833 | 10/2020 |
| WO | WO-2020198832 A1 | 10/2020 |

(Continued)

OTHER PUBLICATIONS

Shah et al., 2010, Supramolecular design of self-assembling nanofibers for cartilage regeneration, PNAS, 107(8): 3293-3298.*
Vas et al., 2015, A Short Peptide That Mimics the Binding Domain of TGF-b1 Presents Potent Anti-Inflammatory Activity, PloS ONE, 10(8): e0136116 (20 pages).*
Zhong et al., 2017, Rational Design of cyclic peptides to disrupt TGF-B/SMAD7 signaling in heterotopic ossification, Journal of Molecular Graphics and Modeling, 72: 25-31.*
Álvarez et al. Bioactive scaffolds with enhanced supramolecular motion promote recovery from spinal cord injury. Science. Nov. 12, 2021;374(6569):848-856.
Andriolo et al. Cell-Free Scaffolds in Cartilage Knee Surgery: A Systematic Review and Meta-Analysis of Clinical Evidence. Cartilage. Jul. 2021;12(3):277-292.

(Continued)

*Primary Examiner* — Amber D Steele
(74) *Attorney, Agent, or Firm* — Casimir Jones, S.C.; Rikki A. Hullinger

(57) ABSTRACT

Provided herein are self-assembling peptide amphiphiles (PAs) comprising a bioactive Transforming growth factor beta 1 (TGF-β1) mimetic epitope, high-aspect-ratio nano-structures of PAs displaying a TGF-β1 mimetic epitope, and methods of enhancing cartilage regeneration/repair and/or treatment of osteoarthritis and other musculoskeletal injuries and diseases.

18 Claims, 26 Drawing Sheets

Specification includes a Sequence Listing.

(56)                References Cited

U.S. PATENT DOCUMENTS

2019/0300574 A1    10/2019    Sharma

FOREIGN PATENT DOCUMENTS

WO    WO-2020198833 A1 *  10/2020    ............. A61K 38/10
WO    WO-2020256287 A2 *  12/2020    ........... A61K 31/015

OTHER PUBLICATIONS

Araujo et al. TGFß1 mimetic peptide modulates immune response to grass pollen allergens in mice. Allergy. Apr. 2020;75(4):882-891.

Beniash et al. Self-assembling peptide amphiphile nanofiber matrices for cell entrapment. Acta Biomater. Jul. 2005;1(4):387-97.

Berns et al. A tenascin-C mimetic peptide amphiphile nanofiber gel promotes neurite outgrowth and cell migration of neurosphere-derived cells. Acta Biomater. Jun. 2016:37:50-8.

Blaney Davidson et al. Reduced transforming growth factor-beta signaling in cartilage of old mice: role in impaired repair capacity. Arthritis Res Ther. 2005;7(6):R1338-47.

Blunk et al. Differential effects of growth factors on tissue-engineered cartilage. Tissue Eng. Feb. 2002;8(1):73-84.

Da Silva et al. Super-resolution microscopy reveals structural diversity in molecular exchange among peptide amphiphile nanofibres. Nat Commun. May 19, 2016:7:11561.

Dasch et al. Monoclonal antibodies recognizing transforming growth factor-beta. Bioactivity neutralization and transforming growth factor beta 2 affinity purification. J Immunol. Mar. 1, 1989;142(5):1536-41.

Dems et al. Multivalent Clustering of Adhesion Ligands in Nanofiber-Nanoparticle Composites. Acta Biomater. Jan. 1, 2021:119:303-311.

Edelbrock et al. Supramolecular Nanostructure Activates TrkB Receptor Signaling of Neuronal Cells by Mimicking Brain-Derived Neurotrophic Factor. Nano Lett. Oct. 10, 2018;18(10):6237-6247.

Erggelet et al. Microfracture for the treatment of cartilage defects in the knee joint—A golden standard ?. J Clin Orthop Trauma. Jul.-Sep. 2016;7(3): 145-52.

Fox et al. The basic science of articular cartilage: structure, composition, and function. Sports Health. Nov. 2009;1(6):461-8.

Ghatak et al. Transforming growth factor ß1 (TGFß1)-induced CD44V6-NOX4 signaling in pathogenesis of idiopathic pulmonary fibrosis. J Biol Chem. Jun. 23, 2017;292(25):10490-10519.

Ghouri et al. Update on novel pharmacological therapies for osteoarthritis. Ther Adv Musculoskelet Dis. Jul. 23, 2019:11:1759720X19864492.

Goldring et al. The control of chondrogenesis. J Cell Biochem. Jan. 1, 2006;97(1):33-44.

Gosal et al. Competing pathways determine fibril morphology in the self-assembly of beta2-microglobulin into amyloid. J Mol Biol. Aug. 26, 2005;351(4):850-64.

Greenfield et al. Computed circular dichroism spectra for the evaluation of protein conformation. Biochemistry. Oct. 1969;8(10):4108-16.

Gresham et al. Growth factor delivery using extracellular matrix-mimicking substrates for musculoskeletal tissue engineering and repair. Bioact Mater. Dec. 24, 2020;6(7):1945-1956.

Hall. The Role of Chondrocyte Morphology and Volume in Controlling Phenotype-Implications for Osteoarthritis, Cartilage Repair, and Cartilage Engineering. Curr Rheumatol Rep. Jun. 15, 2019;21(8):38.

Hartgerink et al. Self-assembly and mineralization of peptide-amphiphile nanofibers. Science. Nov. 23, 2001;294(5547):1684-8.

Hendricks et al. Supramolecular Assembly of Peptide Amphiphiles. Acc Chem Res. Oct. 17, 2017;50(10):2440-2448.

Huey et al. Unlike bone, cartilage regeneration remains elusive. Science. Nov. 16, 2012;338(6109):917-21.

International Search Report and Written Opinion for PCT/US2022/074263 mailed Oct. 22, 2022,.

Jackson et al. The use and misuse of FTIR spectroscopy in the determination of protein structure. Crit Rev Biochem Mol Biol. 1995;30(2):95-120.

Johnston et al. A structurally distinct TGF-ß mimic from an intestinal helminth parasite potently induces regulatory T cells. Nat Commun. Nov. 23, 2017;8(1):1741.

Karsdal et al. Disease-modifying treatments for osteoarthritis (DMOADs) of the knee and hip: lessons learned from failures and opportunities for the future. Osteoarthritis Cartilage. Dec. 2016;24(12):2013-2021.

Koelling et al. Migratory chondrogenic progenitor cells from repair tissue during the later stages of human osteoarthritis. Cell Stem Cell. Apr. 3, 2009;4(4):324-35.

Leifer et al. The burden of OA-health services and economics. Osteoarthritis Cartilage. Jan. 2022;30(1):10-16.

Lewis et al. Transforming Growth Factor ß-1 Binding by Peptide Amphiphile Hydrogels. ACS Biomater Sci Eng. Aug. 10, 2020;6(8):4551-4560.

Li et al. Peptide ligands that use a novel binding site to target both TGF-ß receptors. Mol Biosyst. Dec. 2010;6(12):2392-402.

Li et al. Small Angle X-ray Scattering for Nanoparticle Research. Chem Rev. Sep. 28, 2016;116(18):11128-80.

Liu et al. Functional peptides for cartilage repair and regeneration. Am J Transl Res. Feb. 15, 2018;10(2):501-510.

Loeser. Integrins and chondrocyte-matrix interactions in articular cartilage. Matrix Biol. Oct. 2014:39:11-6.

Lourenço et al. Molecular Structure and Supramolecular Assembly of a TGF-B1 Mimetic Oligopeptide. J. Mol. Struct. 2020. 1219.

Massagué. TGFß signalling in context. Nat Rev Mol Cell Biol. Oct. 2012;13(10):616-30.

Mayo et al. A recipe for designing water-soluble, beta-sheet-forming peptides. Protein Sci. Jul. 1996;5(7):1301-15.

Newcomb et al. Cell death versus cell survival instructed by supramolecular cohesion of nanostructures. Nat Commun. 2014:5:3321.

O'Connell et al. Human chondrocyte migration behaviour to guide the development of engineered cartilage. J Tissue Eng Regen Med. Mar. 2017;11(3):877-886.

Reyes et al. Repair of an osteochondral defect by sustained delivery of BMP-2 or TGFß1 from a bilayered alginate-PLGA scaffold. J Tissue Eng Regen Med. Jul. 2014;8(7):521-33.

Sato et al. Programmable Assembly of Peptide Amphiphile via Noncovalent-to-Covalent Bond Conversion. J Am Chem Soc. Jul. 5, 2017;139(26):8995-9000.

Shah et al. Supramolecular design of self-assembling nanofibers for cartilage regeneration. Proc Natl Acad Sci USA. Feb. 23, 2010;107(8):3293-8.

Shen et al. TGF-ß signaling and the development of osteoarthritis. Bone Res. 2014:2:14002.

Sur et al. Epitope topography controls bioactivity in supramolecular nanofibers. Biomater Sci. Mar. 2015;3(3):520-32.

Tantakitti et al. Energy landscapes and functions of supramolecular systems. Nat Mater. Apr. 2016;15(4):469-76.

Teicher. TGFß-Directed Therapeutics: 2020. Pharmacol Ther. Jan. 2021:217:107666.

Thielen et al. TGFß/BMP Signaling Pathway in Cartilage Homeostasis. Cells. Aug. 24, 2019;8(9):969.

Van Beuningen et al. Transforming growth factor-beta 1 stimulates articular chondrocyte proteoglycan synthesis and induces osteophyte formation in the murine knee joint. Lab Invest. Aug. 1994;71(2):279-90.

Vaz et al. A Short Peptide That Mimics the Binding Domain of TGF-ß1 Presents Potent Anti-Inflammatory Activity. PLoS One. Aug. 27, 2015;10(8):e0136116.

Wakefield et al. Recombinant latent transforming growth factor beta 1 has a longer plasma half-life in rats than active transforming growth factor beta 1, and a different tissue distribution. J Clin Invest. Dec. 1990;86(6):1976-84.

Walker et al. ChondroGELesis: Hydrogels to harness the chondrogenic potential of stem cells. Mater Sci Eng C Mater Biol Appl. Feb. 2021:121:111822.

Wang et al. The restoration of full-thickness cartilage defects with BMSCs and TGF-beta 1 loaded PLGA/fibrin gel constructs. Biomaterials. Dec. 2010;31(34):8964-73.

(56)　　　　　　　References Cited

OTHER PUBLICATIONS

Wang et al. TGFß signaling in cartilage development and mainte-
nance. Birth Defects Res C Embryo Today. Mar. 2014;102(1):37-51.
Wang et al. Biological potential alterations of migratory chondrogenic
progenitor cells during knee osteoarthritic progression. Arthritis Res
Ther. Mar. 27, 2020;22(1):62.
Wipff et al. Integrins and the activation of latent transforming
growth factor beta1—an intimate relationship. Eur J Cell Biol. Sep.
2008;87(8-9):601-15.
Xie et al. Systemic neutralization of TGF-ß attenuates osteoarthritis.
Ann N Y Acad Sci. Jul. 2016;1376(1):53-64.
Yuan et al. Peptide Sequence Determines Structural Sensitivity to
Supramolecular Polymerization Pathways and Bioactivity. J Am
Chem Soc. Sep. 14, 2022;144(36):16512-16523.
Lewis J.A., et al., "Transforming Growth Factor ß-1 Binding by
Peptide Amphiphile Hydrogels", ACS Biomaterials Science and
Engineering, 2020, vol. 6, No. 8, Jul. 8, 2020, pp. 4551-4560,
XP093279820, 10 pages, ISSN: 2373-9878, DOI: 10.1021/
acsbiomaterials.0c00679, abstract, figure 1.
Lourenco T. C. et al: "Molecular Structure and Supramolecular
Assembly of a TGF-Beta1 Mimetic Oligopeptide", Journal of
Molecular Structure, vol. 1219, Nov. 1, 2020, p. 128691, XP093279964,
pp. 1-7, NL ISSN: 0022-2860, DOI: 10.1016/j.molstruc.2020.
128691.
Vaz E.R., et al., "A Short Peptide That Mimics the Binding Domain
of TGF-[beta]1 Presents Potent Anti-Inflammatory Activity", PLOS
ONE, vol. 10, No. 8, Aug. 27, 2014, pp. 1-20, e0136116, XP055746234,
DOI: 10.1371/journal.pone.0136116.

* cited by examiner

FIG. 1A-D a) Backbone PA-a
$C_{16}$-AAEE

Backbone PA-b
$C_{16}$-AEAE

R = b) TGF-β1 PA c) InTGF-β1 PA d) TGF-β1 mimetic epitope
$CESPLKRQC_{cyclic}$

FIG. 2A-J
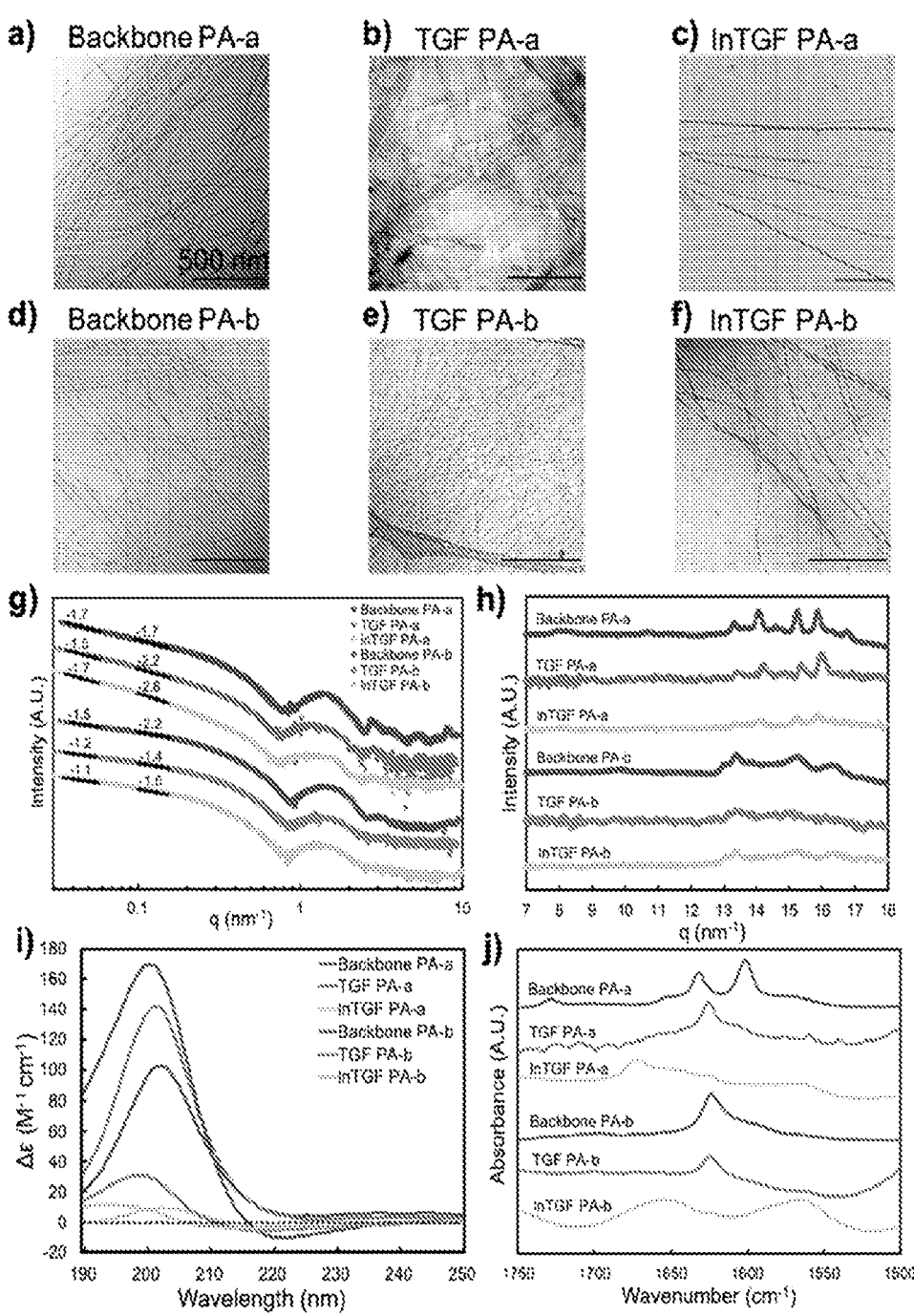

FIG. 3A-C
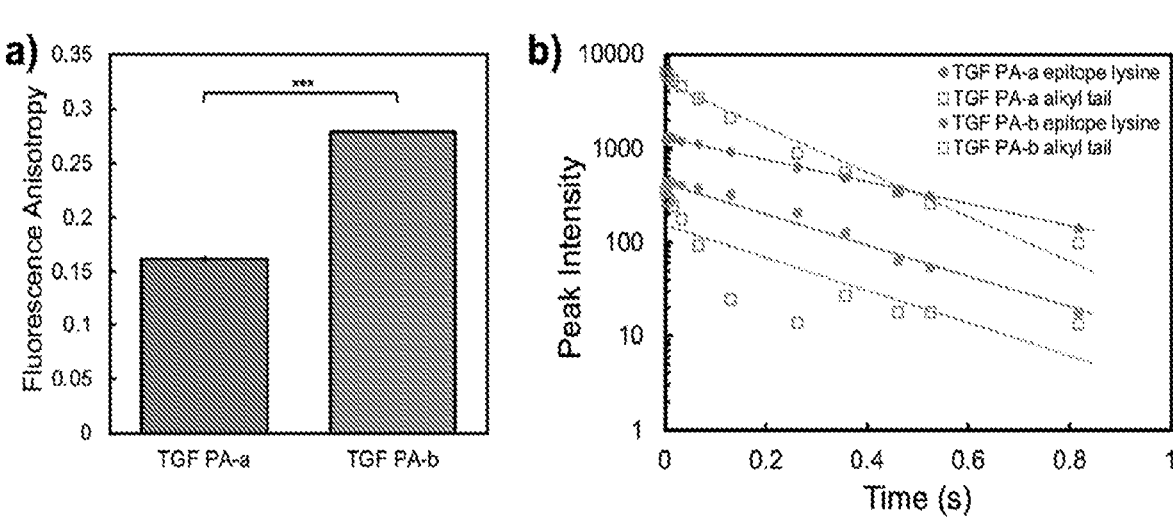
| | Methylene proton of epitope lysine residue | Methyl proton of terminal carbon of alkyl chain |
|---|---|---|
| TGF PA-a | $3.72 \pm 0.16 \ s^{-1}$ | $40.32 \pm 10.38 \ s^{-1}$ |
| TGF PA-b | $2.93 \pm 0.12 \ s^{-1}$ | $8.23 \pm 0.54 \ s^{-1}$ |

FIG. 4A-F
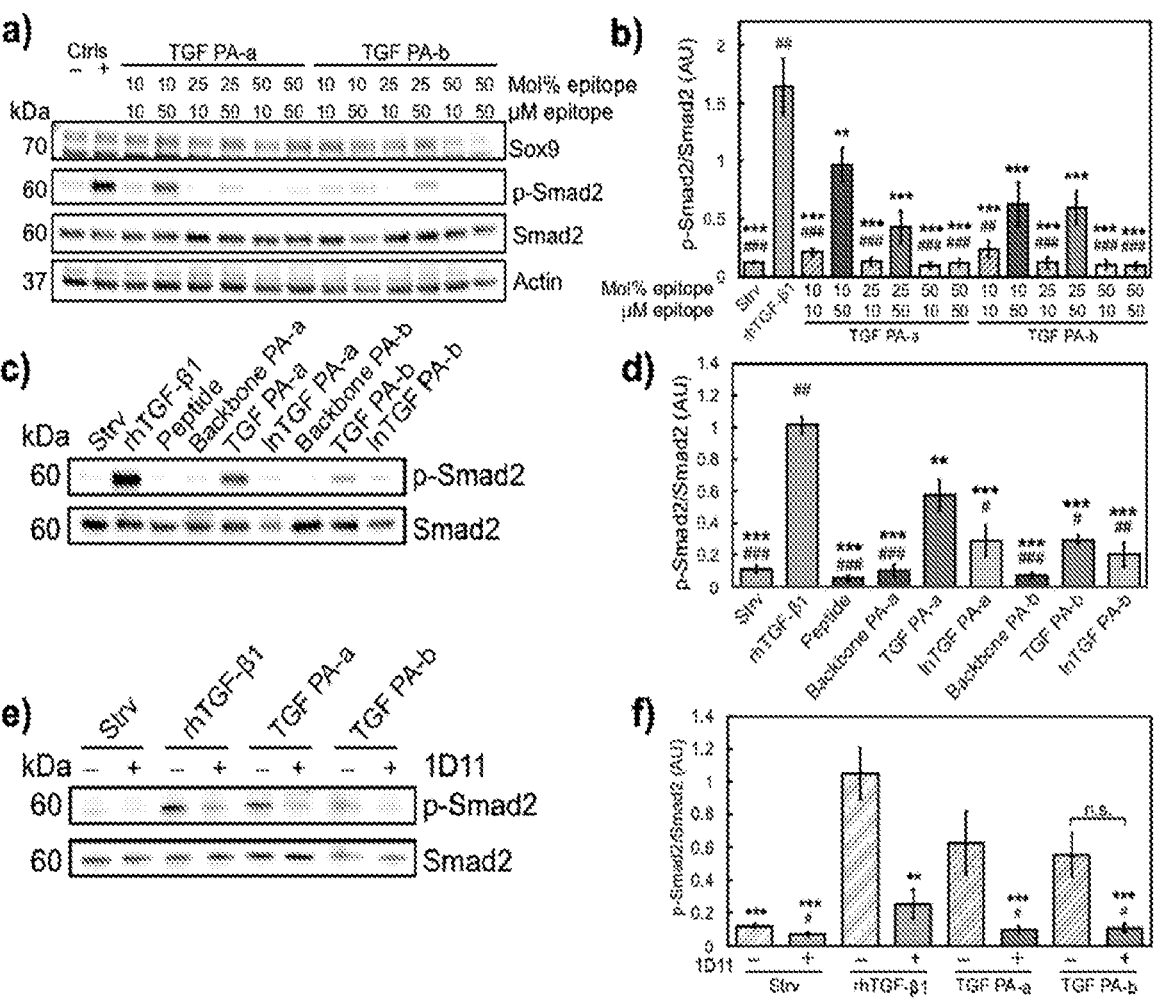

FIG. 5A-E
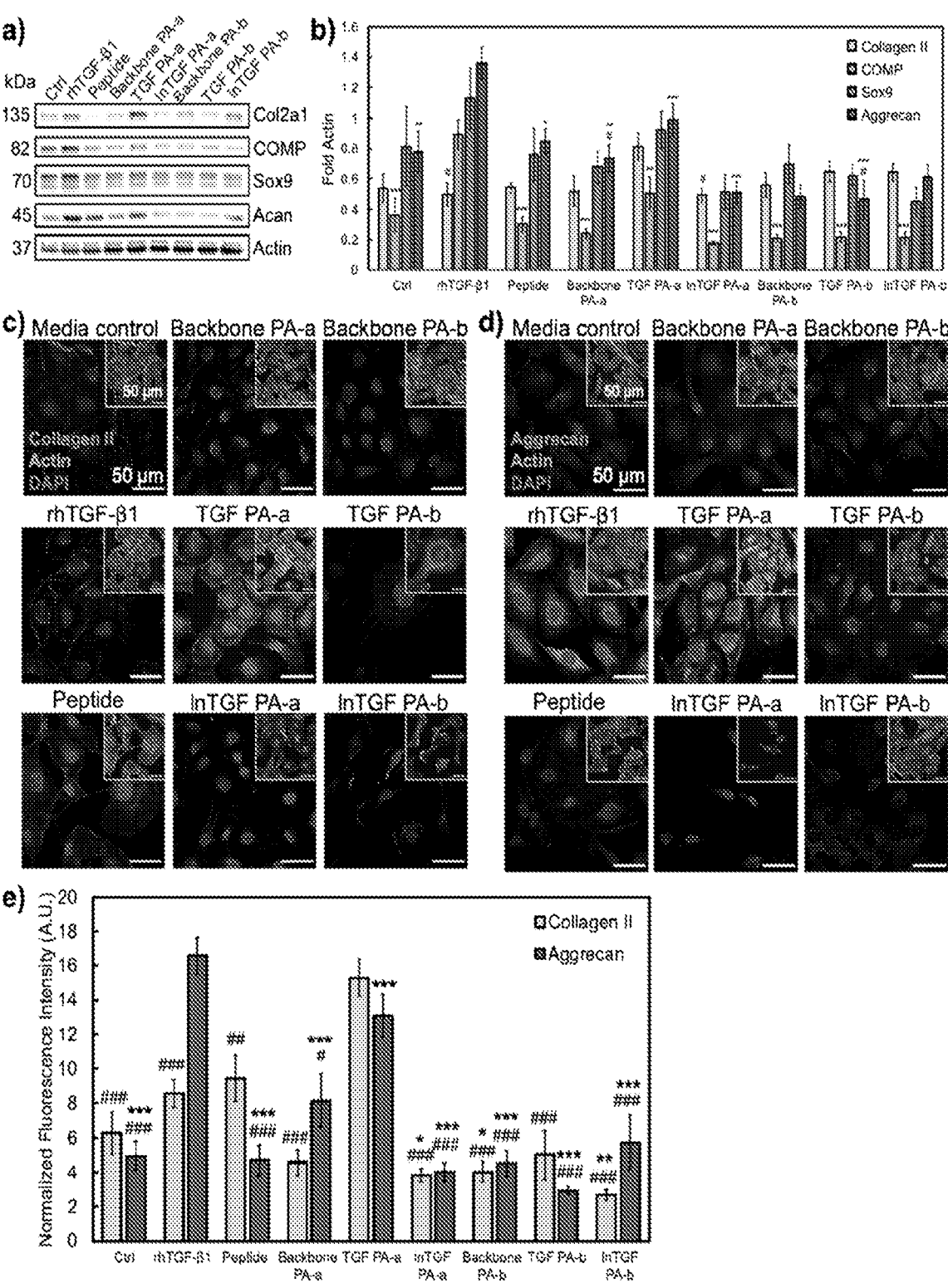

FIG. 6A-G
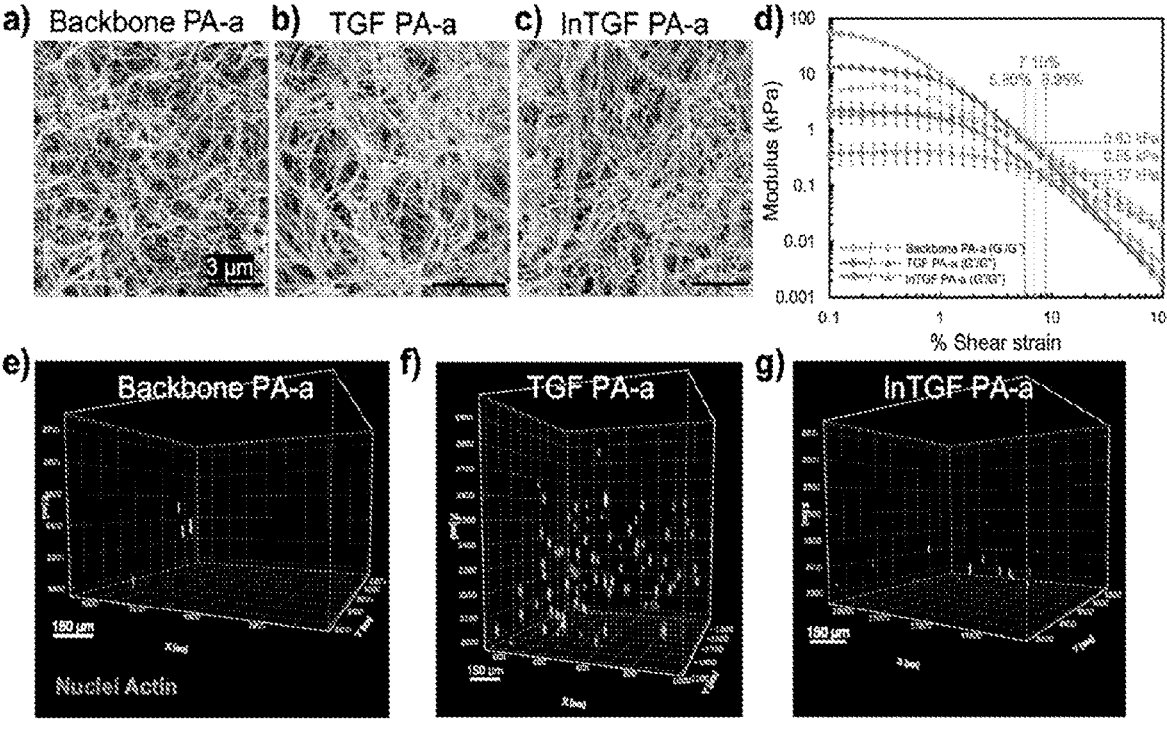

FIG. 17A-B
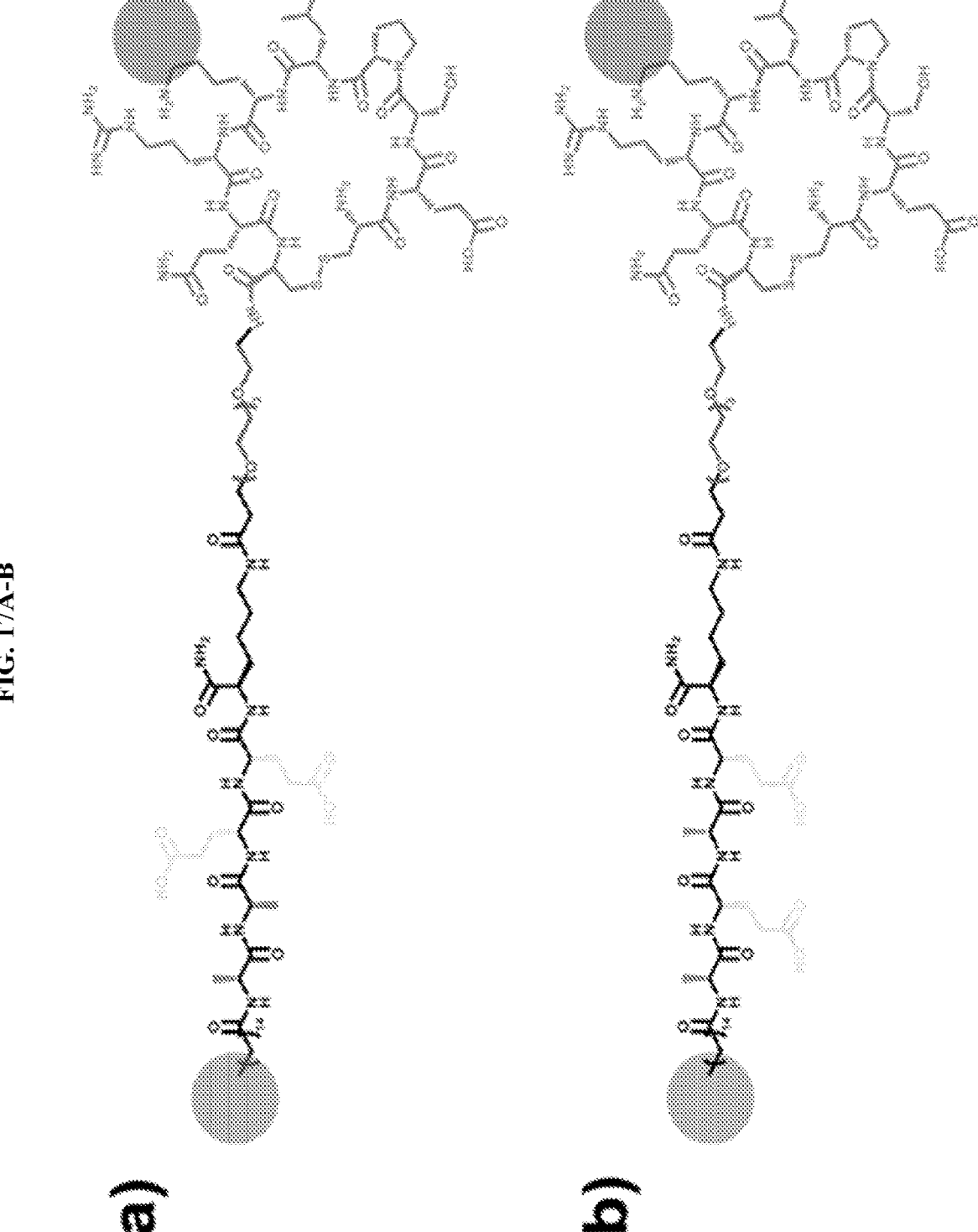
a)
b)

FIG. 20A-B
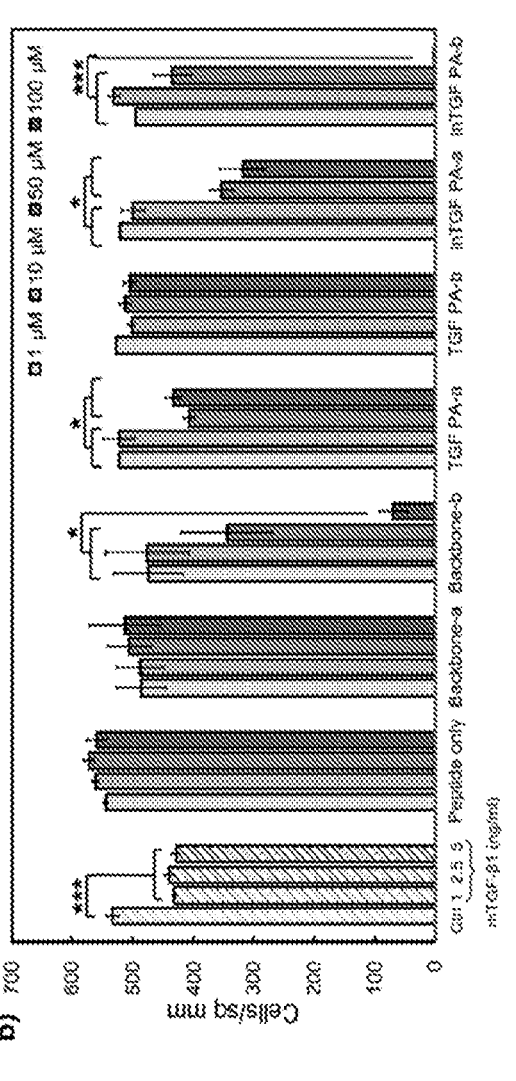

FIG. 21A-B
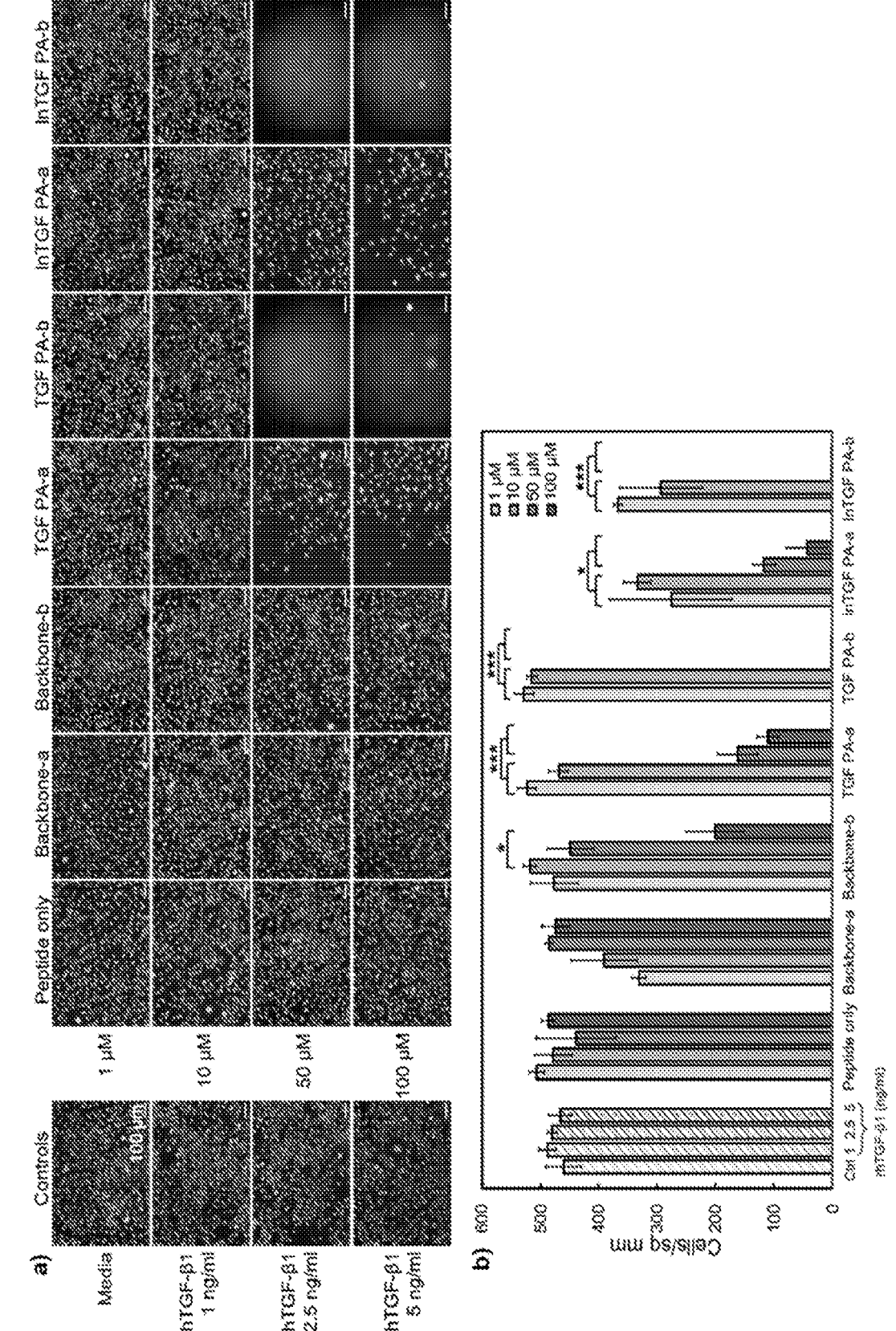

FIG. 24A-F
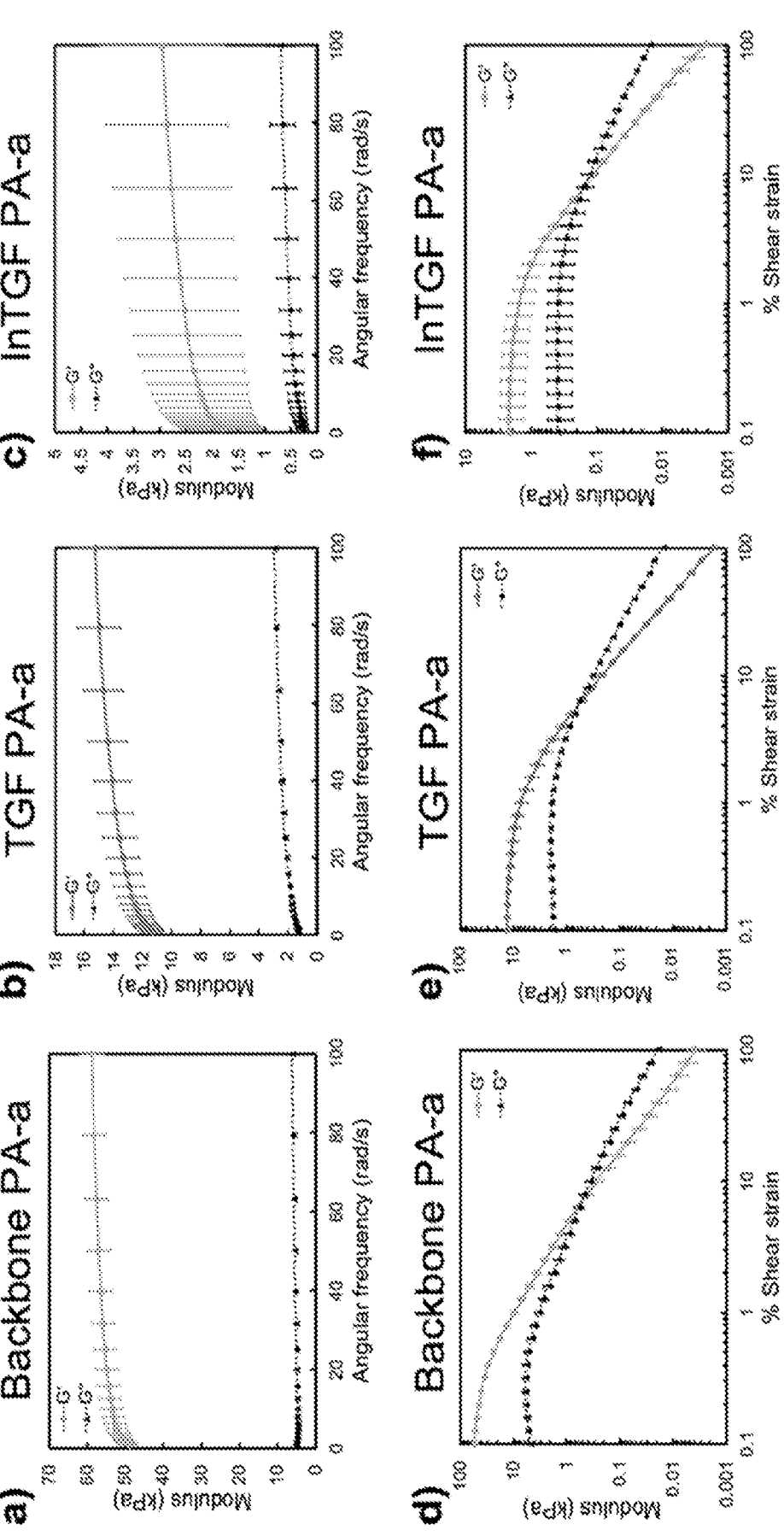

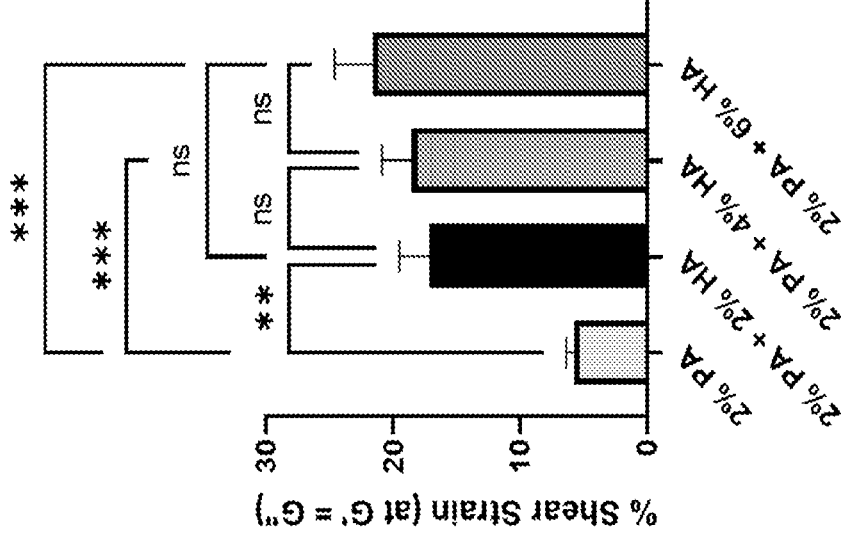
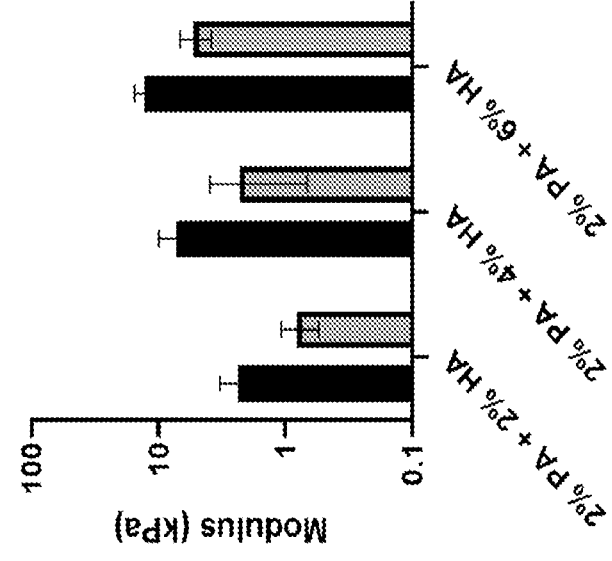
FIG. 25A-B

FIG. 26A-C
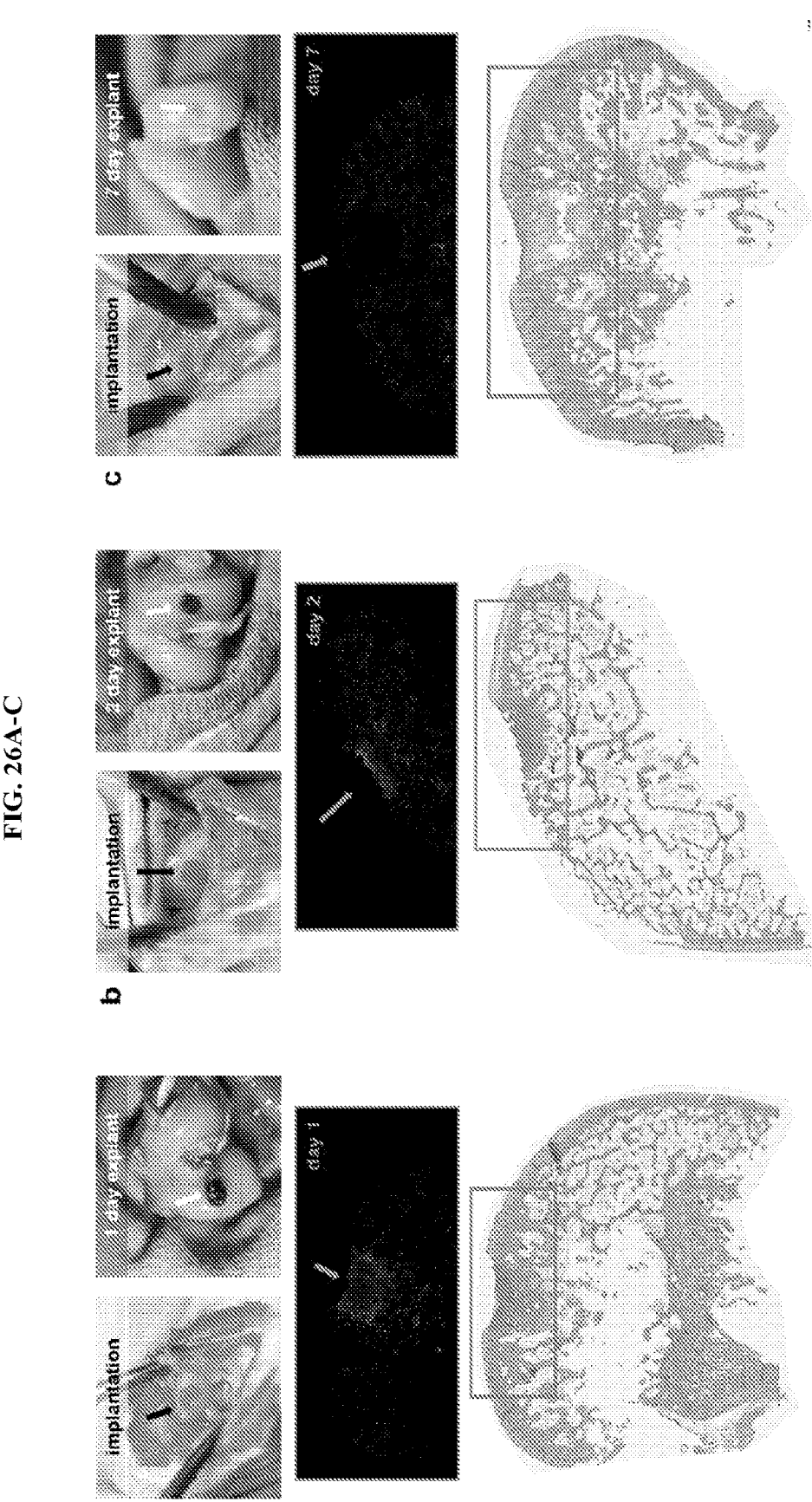

SELF-ASSEMBLING PEPTIDE AMPHIPHILES DISPLAYING A TRANSFORMING GROWTH FACTOR BETA 1 (TGF-β1) MIMETIC EPITOPE

CROSS-REFERENCE TO RELATED APPLICATIONS

The present application is a national stage entry of PCT/US2022/074263, filed Jul. 28, 2022, which claims the benefit of and priority to U.S. Provisional Patent Application Ser. No. 63/227,097, filed Jul. 29, 2021, each of which is hereby incorporated by reference in its entirety.

SEQUENCE LISTING

The text of the computer readable sequence listing filed herewith, titled "39648-252_SEQUENCE_LISTING-Corrected", created Jul. 28, 2025, having a file size of 12,332 bytes, is hereby incorporated by reference in its entirety.

FIELD

Provided herein are self-assembling peptide amphiphiles (PAs) comprising a bioactive Transforming growth factor beta 1 (TGF-β1) mimetic epitope, high-aspect-ratio nanostructures of PAs displaying a TGF-β1 mimetic epitope, and methods of enhancing cartilage regeneration/repair and/or treatment of osteoarthritis and other musculoskeletal injuries and diseases.

BACKGROUND

Cartilage degeneration is one of the most widespread and incurable musculoskeletal disorders. Articular cartilage is integral to joint movement and constantly experiences high stresses and repetitive impact, resulting in degeneration, including osteoarthritis (OA), over time.[1] OA leads to painful functional impairment and comorbidity affecting over 32 million adults in the U.S. with this number predicted to rise with the aging population.[2] Cartilage regeneration faces several unique biological and mechanical challenges that are inadequately addressed by existing treatments, contributing to nationwide direct medical costs of $72 billion.[2] There are currently no licensed disease-modifying OA drugs and current treatments are temporary and palliative rather than regenerative, aiming to slow disease progression or postpone inevitable total joint replacement.[3,4] Although microfracture surgery remains the gold standard to repair cartilage clinically,[5] newer biomaterial and growth factor strategies have recently emerged as promising engineered approaches. However, these strategies often face issues of non-biodegradability, poor mechanical strength, and off-target immunological effects.[6,7] To facilitate cartilage regeneration, biomaterial scaffolds must withstand the mechanical stresses of joint environments, while facilitating biomolecular signaling required for chondrogenic differentiation and maintenance.

SUMMARY

Provided herein are self-assembling peptide amphiphiles (PAs) comprising a bioactive Transforming growth factor beta 1 (TGF-β1) mimetic epitope, high-aspect-ratio nanostructures of PAs displaying a TGF-β1 mimetic epitope, and methods of enhancing cartilage regeneration/repair and/or treatment of osteoarthritis and other musculoskeletal injuries and diseases.

In some embodiments, provided herein are compositions comprising a bioactive peptide amphiphile (PA) comprising: (i) a hydrophobic non-peptidic segment; (ii) a β-sheet-forming peptide segment; (iii) an acidic peptide segment; and (iv) a TGF-β1 mimetic epitope peptide.

In some embodiments, the TGF-β1 mimetic epitope peptide comprises an amino acid sequence having 3 or fewer (e.g., 3, 2, 1, 0) substitutions relative to CESPLKRQC (SEQ ID NO: 1). In some embodiments, the TGF-β1 mimetic epitope peptide comprises at least 50% sequence similarity (e.g. 50%, 60%, 70%, 80%, 90%, 100%, or ranges therebetween) to CESPLKRQC (SEQ ID NO: 1).

In some embodiments, the hydrophobic non-peptidic segment of the bioactive peptide amphiphile comprises an acyl chain. In some embodiments, the acyl chain comprises $C_6$-$C_{20}$ (e.g., $C_6$, $C_8$, $C_{10}$, $C_{12}$, $C_{14}$, $C_{16}$, $C_{18}$, $C_{20}$).

In some embodiments, the β-sheet-forming peptide segment of the bioactive peptide amphiphile comprises a combination of 2-6 V and A residues. In some embodiments, the 0-sheet-forming peptide segment of the bioactive peptide amphiphile and the charged peptide amphiphile is selected from VVVAAA (SEQ ID NO: 3), AAAVVV (SEQ ID NO: 4), AAVV (SEQ ID NO: 5), VVAA (SEQ ID NO: 6), AA, VV, VA, or AV.

In some embodiments, the acidic peptide segment of the bioactive peptide amphiphile comprises a combination of 1-4 Glu (E) and/or Asp (D) residues. In some embodiments, the acidic peptide segment comprises is selected from E, EE, EEE, D, DD, DDD, ED, DE, EDE, DED, EDD, and DEE.

In some embodiments, the bioactive PA comprises a backbone PA selected from C16-AAEE (SEQ ID NO: 7), C16-AEAE (SEQ ID NO: 8), and C16-VVVAAAEEE (SEQ ID NO: 9). In some embodiments, the TGF-β1 mimetic epitope peptide is CESPLKRQC (SEQ ID NO: 1), cyclized via disulfide. In some embodiments, the TGF-β1 mimetic epitope peptide is tethered to the backbone PA by a lysine linker.

In some embodiments, compositions (e.g., nanostructures) herein further comprise a diluent PA comprising: (i) a hydrophobic non-peptidic segment; (ii) a β-sheet-forming peptide segment; and (iii) a charged peptide segment.

In some embodiments, the hydrophobic non-peptidic segment of the diluent peptide amphiphile comprises an acyl chain. In some embodiments, the acyl chain comprises $C_6$-$C_{20}$ (e.g., $C_6$, $C_8$, $C_{10}$, $C_{12}$, $C_{14}$, $C_{16}$, $C_{18}$, $C_{20}$).

In some embodiments, the β-sheet-forming peptide segment of the diluent peptide amphiphile comprises a combination of 2-6 V and A residues. In some embodiments, the (3-sheet-forming peptide segment of the bioactive peptide amphiphile and the charged peptide amphiphile is selected from VVVAAA (SEQ ID NO: 3), AAAVVV (SEQ ID NO: 4), AAVV (SEQ ID NO: 5), VVAA (SEQ ID NO: 6), AA, VV, VA, or AV.

In some embodiments, the acidic peptide segment of the diluent peptide amphiphile comprises a combination of 1-4 Glu (E) and/or Asp (D) residues. In some embodiments, acidic peptide segment comprises is selected from E, EE, EEE, D, DD, DDD, ED, DE, EDE, DED, EDD, and DEE.

In some embodiments, the diluent PA comprises a backbone PA selected from C16-AAEE (SEQ ID NO: 7), C16-AEAE (SEQ ID NO: 8), and C16-VVVAAAEEE (SEQ ID NO: 9).

In some embodiments, compositions (e.g., nanostructures) herein comprise 5%-95% (by mol) bioactive peptide amphiphile and 5% to 95% (by mol) diluent peptide amphiphile. For example 5-95% may include 5%, 10%, 15%, 20%, 25%, 30%, 35%, 40%, 45%, 50%, 55%, 60%, 65%, 70%, 75%, 80%, 85%, 90%, 95%, or ranges therebetween (e.g., 25-75%)).

In some embodiments, provided herein are methods of promoting cartilage repair or regeneration comprising administering a PA nanostructure composition herein to a subject suffering from a cartilage defect or injury.

In some embodiments, provided herein are methods of treating osteoarthritis or a musculoskeletal injuries or disease comprising administering a PA nanostructure composition to a subject suffering from osteoarthritis or a musculoskeletal injuries or disease.

In some embodiments, provided herein are methods of preventing osteoarthritis or a musculoskeletal injuries or disease comprising administering a PA nanostructure composition to a subject at elevated risk for osteoarthritis or a musculoskeletal injuries or disease.

BRIEF DESCRIPTION OF THE DRAWINGS

FIG. 1A-D: Chemical structures of PA and peptide molecules. (a) Backbone PA-a (SEQ ID NO: 7) (top) and Backbone PA-b (SEQ ID NO: 8) (bottom), where R=H, (b) TGF-$\beta$1 mimetic PA, (c) linear ln TGF-$\beta$1 PA, and (d) TGF-$\beta$1 mimetic peptide (SEQ ID NO: 1).

FIG. 2A-J: (a-f) Cryo-TEM micrographs of (a) Backbone PA-a, (b) TGF PA-a, (c) linear ln TGF PA-a, (d) Backbone PA-b, (e) TGF PA-b, and (f) linear ln TGF PA-b nanostructures. Backbone PA nanostructures are assembled at 100 mol % and epitope nanostructures are co-assembled at 10 mol % with diluent backbone PA. (g-j) Structural analysis of Backbone PA, TGF PA, and ln TGF PA nanostructures on each Backbone PA-a (shades of blue) and Backbone PA-b (shades of red) based systems. (g) SAXS patterns, (h) WAXS patterns, (i) CD spectra, and (j) FTIR spectra. All PA solutions were dissolved in water at 12 mM total PA, 30 mM NaCl, and pH 6.8. (***, p<0.001).

FIG. 3A-C: Analysis of supramolecular dynamics of TGF-$\beta$1 mimetic PA assemblies, where TGF PA molecules are co-assembled at 10 mol % with diluent backbone PA molecules. (a) Fluorescence anisotropy of TGF PA-a and TGF PA-b assemblies with TAMRA-labeled TGF-$\beta$1 mimetic epitopes. (b) $^1$H NMR spectra peak intensities as a function of time and regression lines for TGF PA-a and TGF PA-b assemblies. (c) $^1$H spin-lattice relaxation rates of protons in TGF PA-a and TGF PA-b assemblies.

FIG. 4A-F: Smad2 activation and downstream TGF-$\beta$1 pathway analysis in human chondrocytes treated with TGF PA. (a) Western blot of Sox9, phosphorylated Smad2 (p-Smad2), Smad2, and actin in chondrocytes treated with TGF PA-a and TGF PA-b at a range of co-assembly ratios and concentrations for 4 h in vitro. TGF-$\beta$1 protein (rhTGF-$\beta$1) and starvation media (Strv) were used as positive and negative controls, respectively. (b) Quantitative densitometry analysis of western blot data from (a) showing the fraction of Smad2 that is phosphorylated (*, vs rhTGF-$\beta$1; #, vs 10% TGF PA-a 50 µM). (c) Western blot of p-Smad2 and Smad2 in chondrocytes treated with Strv, rhTGF-$\beta$1, TGF mimetic peptide, and different PA conditions (backbone PA, TGF mimetic PA, and linear ln TGF PA) for 4 h in vitro. (d) Quantitative densitometry analysis of western blot data from (c) showing the fraction of Smad2 that is phosphorylated (*, vs rhTGF-$\beta$1; #, vs TGF PA-a). (e) Western blot of p-Smad2 and Smad2 in chondrocytes treated with Strv, rhTGF-$\beta$1, TGF PA-a and TGF PA-b, each without (−) and with (+) the addition of pan-TGF-$\beta$ neutralizing antibody 1D11. (f) Quantitative densitometry analysis of western blot data from (e) showing the fraction of Smad2 that is phosphorylated (*, vs rhTGF-$\beta$1-1D11; #, TGF PA-a $\beta$1-1D11). (#, p<0.05; /##, p<0.01, */###, p<0.001).

FIG. 5A-E: ECM protein synthesis in human chondrocytes treated with TGF PA. (a) Western blot of collagen II, cartilage oligomeric matrix protein (COMP), Sox9, and aggrecan in chondrocytes treated with Ctrl, rhTGF-$\beta$1, TGF mimetic peptide, and different PA conditions (backbone PA, TGF mimetic PA, and linear TGF PA) for three days in vitro. (b) Quantitative densitometry analysis of western blot data from (a) showing the fraction of each ECM protein normalized to actin (*, vs rhTGF-$\beta$1; #, TGF PA-a). (c-d) Fluorescence micrographs of human chondrocytes treated with Ctrl, rhTGF-$\beta$1, TGF mimetic peptide, and different PA conditions (backbone PA, TGF mimetic PA, and linear TGF PA) for three days in vitro. Cells were stained for collagen II (red) in (c), aggrecan (red) in (d), F-actin (green), and DAPI (nuclei, blue). (e) Fluorescence intensity quantification of collagen II and aggrecan from ICC micrographs in (c-d) (*, vs rhTGF-$\beta$1; #, TGF PA-a). (*/#, p<0.05; , p<0.01, */###, p<0.001).

FIG. 6A-G: Mechanical characterization of PA hydrogels and chondrogenic behavior of human chondrocytes encapsulated in hydrogels. (a-c) SEM micrographs of (a) Backbone PA-a only, (b) TGF PA-a, and (c) ln TGF PA-a PA gels. (d) Storage and loss moduli as a function of strain for PA gels of Backbone PA-a only, TGF PA-a, and ln TGF PA-a, with flow strains and moduli indicated by vertical and horizontal lines, respectively. (e-g) Human chondrocytes encapsulated in PA hydrogels. Three-dimensional z-stack reconstructions of cells encapsulated in (e) Backbone PA-a gels, (f) TGF PA-a gels (g) and ln TGF PA-a gels after three days in vitro. Cells were stained for F-actin (green) and nuclei (red), and regions of overlay between F-actin and nuclei appear as yellow.

Figure 16A:
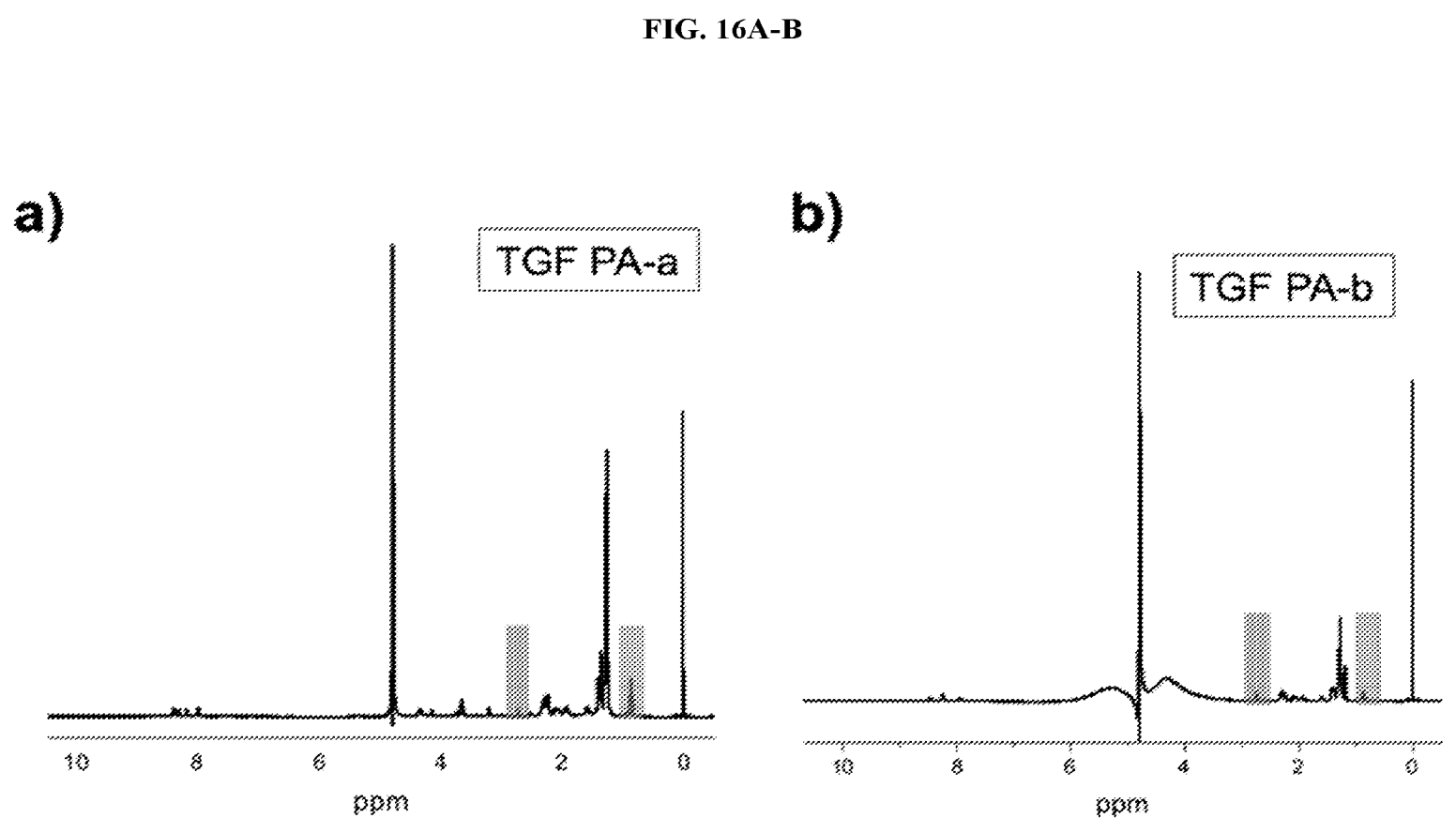

FIG. 16A-B: $^1$H NMR spectra for the protons in (a) TGF PA-a, and (b) TGF PA-b. Methylene protons of epitope lysine residue are indicated in red and methyl protons of terminal carbon of alkyl chain are indicated in blue.

FIG. 17A-B: Locations of protons used in T2-NMR for (a) TGF PA-a (backbone PA-a (SEQ ID NO: 7) conjugated to cyclic TGF-β1 mimetic peptide (SEQ ID NO: 1) by a linker, and (b) TGF PA-b (backbone PA SEQ ID NO: 8) conjugated to cyclic TGF-β1 mimetic peptide (SEQ ID NO: 1) by a linker. Methylene protons of epitope lysine residue are indicated in red and methyl protons of terminal carbon of alkyl chain are indicated in blue.

FIG. 18A-B: Viability assay testing biocompatibility of TGF PA-a and TGF PA-b at a range of co-assembly ratios and concentrations. TGF-β1 protein (rhTGF-β1) and growth media were used as controls. (a) Fluorescence micrographs of cells treated for 24 h in vitro followed by staining for Calcein AM (green, live) and propidium iodide (red, dead). (b) Quantification of cell survival based on cells/mm$^2$ (#, vs. media control). (*, $p<0.05$; ##, $p<0.01$)

FIG. 19A-B: Viability assay testing biocompatibility of TGF PA-a and TGF PA-b at a range of co-assembly ratios and concentrations. TGF-β1 protein (rhTGF-β1) and growth media were used as controls. (a) Fluorescence micrographs of cells treated for 3 days in vitro followed by staining for Calcein AM (green, live) and propidium iodide (red, dead). (b) Quantification of cell survival based on cells/mm$^2$ (#, vs. media control; ^, vs. 10% TGF PA-a 10 μM). (*/#/^, $p<0.05$; /##/^^, $p<0.01$; */###/^^^, $p<0.001$).

FIG. 20A-B: Viability assay testing biocompatibility of different PA conditions (TGF mimetic peptide, backbone, TGF mimetic PA 10 mol % co-assembly, and linear ln TGF PA 10 mol % co-assembly) at a range of concentrations. TGF-β1 protein (rhTGF-β1) and growth media were used as controls. (a) Fluorescence micrographs of cells treated for 24 h in vitro followed by staining for Calcein AM (green, live) and propidium iodide (red, dead). (b) Quantification of cell survival based on cells/mm$^2$. (*, $p<0.05$; , $p<0.01$; *, $p<0.001$)

FIG. 21A-B: Viability assay testing biocompatibility of different PA conditions (TGF mimetic peptide, backbone, TGF mimetic PA 10 mol % co-assembly, and linear ln TGF PA 10 mol % co-assembly) at a range of concentrations. TGF-β1 protein (rhTGF-β1) and growth media were used as controls. (a) Fluorescence micrographs of cells treated for 3 days in vitro followed by staining for Calcein AM (green, live) and propidium iodide (red, dead). (b) Quantification of cell survival based on cells/mm$^2$. (*, $p<0.05$; , $p<0.01$; *, $p<0.001$)

FIG. 24A-F: Rheological analysis of Backbone PA-a (a, d), TGF PA-a (b, e), and ln TGF PA-a gels (c, f). (a-c) Frequency sweep showing the storage modulus (G') and loss modulus (G") for angular frequencies ranging from 0-100 rad/s. (d-f) Strain sweep showing the storage modulus (G'), and loss modulus (G") at shear strains ranging from 0-100%.

FIG. 25A-B: Mechanical properties of hybrid TGF PA gels. (a) Storage (G') and loss (G") modulus of TGF PA-a slurries with varying concentrations of crosslinked HA particles. (b) Strain required to fracture TGF PA-a hydrogels as defined by the crossover point when G'=G" (, $p<0.01$; *, $p<0.001$).

FIG. 26A-C: Implantation of TGF-mimetic PA slurries in a rabbit osteochondral defect model. Following implantation in the medial condyle, slurry retention was tracked using dye-labeled PA molecules after (a) 1, (b) 2, and (c) 7 days post-operation. Fluorescent imaging (middle row) and H&E staining (bottom row) of histological sections of the condyle revealed good implant integration and biodegradation as new cartilage is formed.

DEFINITIONS

Figure 7:
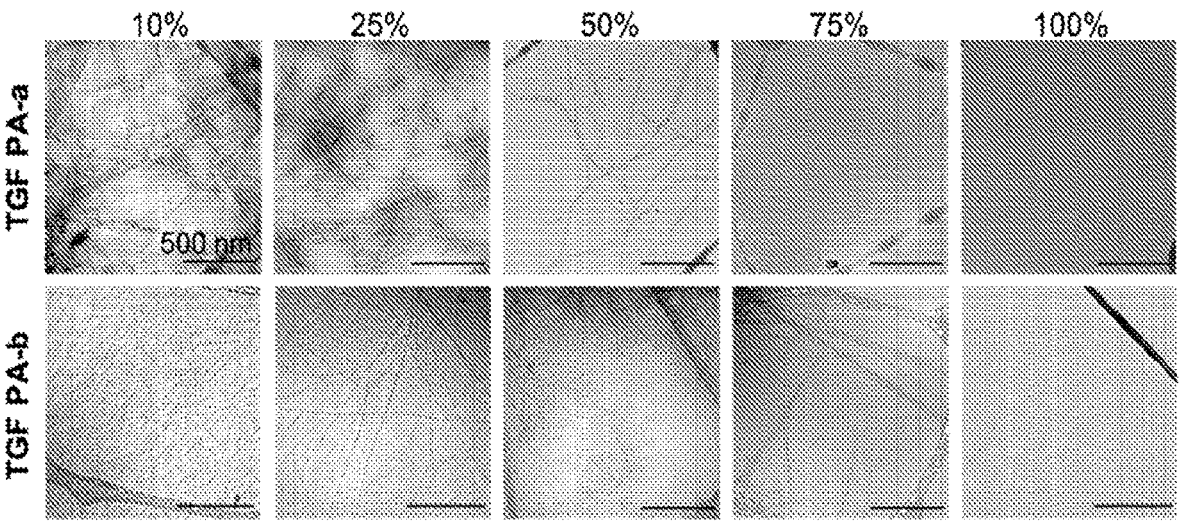
FIG. 7: Cryo-TEM micrographs of TGF PA-a (top) and TGF PA-b (bottom) co-assembled with diluent Backbone PA-a and Backbone PA-b, respectively, at 10, 25, 50, 75, and 100 mol %.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);

4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a bioactive segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a bioactive segment (e.g., linker segment).

As used herein and in the appended claims, the term "lipophilic moiety" or "hydrophobic moiety" refers to the moiety (e.g., an acyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F))

selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "bioactive peptide" refers to amino acid sequences that mediate the action of sequences, molecules, or supramolecular complexes associated therewith. Peptide amphiphiles and structures (e.g., nanofibers) bearing bioactive peptides (e.g., a TGF-β1 mimetic peptide, etc.) exhibits the functionality of the bioactive peptide.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the terms "treat," "treatment," and "treating" refer to reducing the amount or severity of a particular condition, disease state (e.g., osteoarthritis, a cartilage injury, etc.), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and preventing" refer to reducing the likelihood of a particular condition or disease state (e.g., osteoarthritis, a cartilage degradation, etc.) from occurring in a subject not presently experiencing or afflicted with the condition or disease state. The terms do not necessarily indicate complete or absolute prevention. For example "preventing osteoarthritis" refers to reducing the likelihood of osteoarthritis occurring in a subject not presently experiencing or diagnosed with osteoarthritis. In order to "prevent osteoarthritis" a composition or method need only reduce the likelihood of osteoarthritis, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject (e.g., a PA nanostructure displaying a TGF-β1 mimetic peptide and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent (s), and/or when co-administration of two or more agents results in sensitization of a subject to beneficial effects of one of the agents via co-administration of the other agent.

DETAILED DESCRIPTION

Provided herein are self-assembling peptide amphiphiles (PAs) comprising a bioactive Transforming growth factor beta 1 (TGF-β1) mimetic epitope, high-aspect-ratio nanostructures of PAs displaying a TGF-β1 mimetic epitope, and methods of enhancing cartilage regeneration/repair and/or treatment of osteoarthritis and other musculoskeletal injuries and diseases.

The technology comprises peptide amphiphile (PA) molecules and supramolecular PA nanostructures that mimic the chondrogenic activity of TGF-β1 for cartilage regeneration. Bioactive PA molecules conjugated to the TGF-β1 mimetic epitope can be co-assembled with diluent epitope-free molecules for self-assembly into high-aspect-ratio nanostructures presenting bioactive TGF-β1 mimetic domains on their surfaces. These nanostructures enhance cellular signaling and chondrogenic responses through the favorable presentation of the epitope on PA nanostructures. These bioactive PA systems can enhance cartilage regeneration and repair without additional exogenous growth factor and can be used as cell-free regenerative scaffolds to treat osteoarthritis and other musculoskeletal injuries and diseases.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH2, and —NH2.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a., nanofibers)) that bury the lipophilic segment in their core and display the bioactive peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 5), AAAVVV (SEQ ID NO: 4), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C=O groups (e.g., $CH2(O(CH_2)_2NH$, $CH2(O(CH_2)_2)_2NHCO(CH_2)_2CCH$, etc.). In some embodiments, a spacer or linker further comprises additional bioactive groups, substituents, branches, etc.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA (SEQ ID NO: 6); and (c) a charged segment (e.g., comprising KK, EE, etc.). In some embodiments, any PAs within the scope described herein, comprising the components described herein, or within the skill of one in the field, may find use herein.

In some embodiments, peptide amphiphiles comprise a bioactive moiety (e.g., TGF-β1 mimetic epitope). In particular embodiments, a bioactive moiety is the most C-terminal or N-terminal segment of the PA. In some embodiments, the bioactive moiety is attached to the end of the charged segment. In some embodiments, the bioactive moiety is exposed on the surface of an assembled PA structure (e.g., nanofiber). A bioactive moiety is typically a peptide (e.g., TGF-β1 mimetic epitope, etc.), but is not limited thereto. In some embodiments, a bioactive moiety is a peptide sequence that binds a peptide or polypeptide of interests, for example, a growth factor. In some embodiments, a TGF-β1 mimetic epitope is provided as a PA bioactive moiety. In some embodiments, such TGF-β1 mimetic epitopes comprise at least 70% (e.g., 70%, 75%, 80%, 85%, 90%, 95%, 98%, 99%, or ranges therebetween) sequence identity with SEQ ID NO: 1 (CESPLKRQC). In some embodiments, the TGF-β1 mimetic epitope peptide is cyclized. In some embodiments, a TGF-β1 mimetic epitope is SEQ ID NO: 1. In some embodiments, nanofibers are provided comprising bioactive PAs displaying one or more of a peptide comprising at least 70% (e.g., 70%, 75%, 80%, 85%, 90%, 95%, 98%, 99%, or ranges therebetween) sequence identity with one of SEQ ID NO: 1. In some embodiments, a bioactive peptide comprises conservative or semi-conservative substitutions relative to one of SEQ ID NO: 1.

In some embodiments, a peptide amphiphile comprises: (a) a hydrophobic tail comprising an alkyl chain of 8-24 carbons; (b) a structural segment (e.g., comprising VVAA (SEQ ID NO: 6), AAVV (SEQ ID NO: 5), VA, AV, AA, etc.); (c) a charged segment (e.g., comprising KK, EE, EK, KE, EEE, etc.), and a bioactive peptide (e.g., TGF-β1 mimetic epitope). In some embodiments, a PA further comprises an attachment segment or residue (e.g., K) for attachment of the hydrophobic tail to the peptide portion of the PA. In some embodiments, the hydrophobic tail is attached to a lysine side chain. In some embodiments, a PA further comprises an attachment segment or residue (e.g., K) for attachment of the bioactive peptide to the structural segment.

In some embodiments, a peptide amphiphile comprises (e.g., from C-terminus to N-terminus or from N-terminus to C-terminus): bioactive peptide (e.g., TGF-β1 mimetic epitope)—charged segment (e.g., comprising KK, EE, EK, KE, EEE, etc.)—structural segment (e.g., comprising VVAA (SEQ ID NO: 6), AAVV (SEQ ID NO: 5), VA, AV, AA, etc.)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TGF-β1 mimetic epitope)—charged segment (e.g., comprising KK, EE, EK, KE, EEE, etc.)—structural segment (e.g., comprising VVAA (SEQ ID NO: 6), AAVV (SEQ ID NO: 5), VA, AV, AA, etc.)—attachment segment or peptide (e.g., K)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TGF-β1 mimetic epitope)—attachment segment or peptide (e.g., K)—charged segment (e.g., comprising KK, EE, EK, KE, EEE, etc.)—structural segment (e.g., comprising VVAA (SEQ ID NO: 6), AAVV (SEQ ID NO: 5), VA, AV, AA, etc.)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TGF-β1 mimetic epitope)—EEEAAAVVV (SEQ ID NO: 10)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TGF-β1 mimetic epitope)—EEAA (SEQ ID NO: 11)—hydrophobic tail (e.g., comprising an alkyl chain of 8-24 carbons).

In some embodiments, provided herein are nanofibers and nanostructures assembled from the peptide amphiphiles described herein. In some embodiments, a nanofiber is prepared by the self-assembly of the PAs described herein. In some embodiments, a nanofiber comprises or consists of PAs displaying a TGF-β1 mimetic epitope. In some embodiments, the TGF-β1 mimetic epitope is displayed on the surface of the nanofiber. In some embodiments, in addition to PAs displaying a TGF-β1 mimetic epitope, filler PAs are included in the nanofibers. In some embodiments, filler PAs are peptide amphiphiles, as described herein (e.g., structural segment, charged segment, hydrophobic segment, etc.), but lacking a bioactive moiety. In some embodiments, filler peptides are basic or acidic peptides lacking a bioactive moiety (e.g., V3A3K3 (SEQ ID NO: 12), V3A3E3 (SEQ ID NO: 13), etc.). In some embodiments, the filler PAs and TGF-β1 mimetic epitope PAs self-assemble into a nanofiber comprising both types of PAs. In some embodiments, nanostructures (e.g., nanofibers) assembled from the peptide amphiphiles described herein are provided.

In some embodiments, nanostructures are assembled from (1) PAs bearing a bioactive moiety (e.g., TGF-β1 mimetic epitope) and (2) filler PAs (e.g., acidic or basic PAs not-labeled or not displaying a bioactive moiety, etc.). In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) TGF-β1 mimetic epitope PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) acidic filler PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) basic filler PAs. In some embodiments, the ratio of TGF-β1 mimetic epitope PA to acidic and/or basic PAs in a nanofiber determines the mechanical characteristics (e.g., liquid or gel) of the nanofiber material and under what conditions the material will adopt various characteristics (e.g., gelling upon exposure to physiologic conditions, liquifying upon exposure to physiologic conditions, etc.).

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a filler PA (e.g., without a peptide epitope or other nanofiber surface displayed moiety). In some embodiments, at least 0.25 mg/mL of the solution is a filler PA. In some embodiments, a filler PA is a non-bioactive PA molecule having highly charged glutamic acid residues on the terminal end of the molecule (e.g., surface-displayed end). These negatively charged PAs allow for the gelation to take place between nanofibers via ionic crosslinks. In some embodiments, a filler PA is a non-bioactive PA molecule having highly charged lysine residues on the terminal end of the molecule (e.g., surface-displayed end). These positively charged PAs allow for the gelation to take place under basic conditions. The filler PAs provide the ability to incorporate other bio-active PA molecules into the nanofiber matrix while still ensuring the ability of the nanofibers solution to gel. In some embodiments, the solutions are annealed for increased viscosity and stronger gel mechanics. These filler PAs have sequences are described in, for example, U.S. Pat. No. 8,772,228 (e.g., $C_{16}$-VVVAAAEEE (SEQ ID NO: 9)), which is herein incorporated by reference in its entirety.

In some embodiments, the PA nanofiber described herein exhibit a small cross-sectional diameter (e.g., <25 nm, <20 nm, <15 nm, about 10 nm, etc.). In some embodiments, the small cross-section of the nanofibers (~10 nm diameter) allows the fibers to permeate the brain parenchyma.

In some embodiments, the PAs and nanostructures described herein find use in the treatment or prevention of osteoarthritis, cartilage injuries/degradation, and other musculoskeletal injuries and diseases.

In some embodiments, the TGF-β1 mimetic epitope PA nanostructure compositions herein are formulated for delivery to a subject. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, TGF-β1 mimetic epitope PA nanostructure compositions are administered parenterally. In some embodiments, parenteral administration is by intrathecal administration, intracerebroventricular administration, or intraparenchymal administration.

The TGF-β1 mimetic epitope PA nanostructure compositions herein can be administered as the sole active agent or in combination with other pharmaceutical agents such as other agents used in the treatment of osteoarthritis, cartilage injuries/degradation, and other musculoskeletal injuries and diseases.

In some embodiments, the PA nanostructures herein are provided as a composite material with one or more additional components. In some embodiments, a composite herein comprises the PA nanostructure and a biocompatible polymer. In some embodiments, the biocompatible polymer is in the form of particles (e.g., microparticles (e.g., diameters of great than 1 μm but less than 1 mm), nanoparticles (e.g., diameters of great than 1 nm but less than 1 μm), etc.). In some embodiments, the composite is in the form of a slurry, paste, gel, etc.

Suitable biocompatible polymers for use in the materials herein are selected from the group consisting of: PLA, PLLA, PGA, PGLA, PCL, chitosan, polylactides, polyglycolides, epsilon-caprolactone, polyhydroxyvaleric acid, polyhydroxybutyric acid, other polyhydroxy acids, polytrimethylene carbonate, polyamines, vinyl polymers, polyacrylic acids and their derivatives containing ester, polyethylene glycols, polydioxanones, polycarbonates, polyacetals, polyorthoesters, polyamino acids, polyphosphoesters, polyesteramides, polyfumerates, polyanhydrides, polycyanoacrylates, polyoxamers, polyurethanes, polyphosphazenes, aliphatic polyesters, poly(amino acid), copoly(ether-ester), polyakylene oxalate, polyamides, poly(iminocarbonate), polyoxaester, polyamidoesters, amine group-containing polyoxaester, polyacetal, polyalkanoate, gelatin, collagen, elastine, polysaccharide, alginate, chitin, hyaluronic acid, and combinations thereof.

In some embodiments, particles are of any suitable size and shape. In some embodiments, particles are microparticles and have mean diameters of between 1 μm and 1 mm (e.g., 1 μm, 2 μm, 5 μm, 10 μm, 20 μm, 30 μm, 40 μm, 50 μm, 60 μm, 70 μm, 80 μm, 90 μm, 1 mm, or ranges therebetween). In some embodiments, particles are nanoparticles and have mean diameters of between 1 nm and 1 μm (e.g., 1 nm, 2 nm, 5 nm, 10 nm, 20 nm, 30 nm, 40 nm, 50 nm, 60 nm, 70 nm, 80 nm, 90 nm, 1 nm, or ranges therebetween). In some embodiments, particles are generated using any suitable techniques, such as, freezing (e.g., under liquid $N_2$), drying, freeze drying, lyophilizing, grinding, milling, exposure to solvent (e.g., ethanol), sieving, and combinations thereof.

In an exemplary embodiment, the biocompatible particles and peptide amphiphile solution are mixed at 5 wt % biocompatible particles and 1 wt % PA in neutral pH water. Other ranges (e.g., 1 wt %-20 wt % (e.g., 1, 2, 3, 4, 5, 6, 7, 8, 9 10, 11, 12, 13, 14, 15, 16, 17, 18, 19, 20, or any ranges there between) biocompatible particles; 0.1 wt %-10 wt % (e.g., 0.1, 0.2, 0.3, 0.4, 0.5, 0.6, 0.7, 0.8, 0.9, 1, 2, 3, 4, 5, 6, 7, 8, 9 10, or any ranges there between) PAs) may be employed. In particular embodiments, the polymer (e.g., HA) is used from 0 wt % to 20 wt %, and the PAs are used at 0.05 wt % to 3 wt %.

EXPERIMENTAL

Example 1

In vitro characterization of TGF-β1 Mimetic Supramolecular Nanostructures

Materials and Methods

PA Synthesis and Purification

All PA molecules were synthesized using standard fluorenylmethoxycarbonyl (Fmoc) synthesis on Wang resin (EMD Biosciences). The PAs were purified by reverse phase high-performance liquid chromatography (HPLC). The mass spectra for each fraction of PA after HPLC purification was verified using direct injected Q-ToF MS on an Agilent model 6520. The purity of the PAs was confirmed by liquid chromatography-electrospray ionization mass spectrometry (LCMS) using a Phenomenex Gemini C18 column over a 5% to 95% water to acetonitrile gradient with 0.1% ammonium hydroxide.

The TGF-β1 mimetic PA molecule was synthesized using Fmoc-Lys(Mtt)-OH lysine residue on resin with orthogonal protecting groups. Following Fmoc deprotection, the PA backbone, either $C_{16}$-AAEE (SEQ ID NO: 7) or $C_{16}$-AEAE (SEQ ID NO: 8), was synthesized from C- to N-terminus off the lysine α-amino group. Following Mtt deprotection, the $PEG_4$ was synthesized off the lysine sidechain amine, followed by the TGF-β1 mimetic epitope, which was cyclized via disulfide bonding on resin. Following synthesis, the peptides were purified with high-performance liquid chromatography and liquid chromatography mass spectrometry to ensure cyclization of the peptide.

The purified confirmed fractions of each PA were pooled, and solutions were frozen and dried via lyophilization. Diluent backbone PAs were co-assembled with their respective TGF-β1 mimetic PA or linearized epitope PA at different molar percentages by dissolving the lyophilized powders in sterile water. The PA solutions were adjusted to a pH of 7 using a sterile filtered solution of 1 M NaOH and then bath sonicated for 30 minutes. The solutions were thermally annealed at 80° C. for 30 minutes then cooled at a rate of 1° C. per minute to 25° C. The solutions were then adjusted to 30 mM NaCl using a sterile solution of 150 mM NaCl, and then annealed at 50° C. for 30 minutes and cooled.

PA Gel Preparation

Gels were made using 2 wt % PA solutions prepared as previously described, using 10 mol % co-assemblies of epitope PA with diluent PA. 12-well chamber slides (Ibidi) were coated with 0.01 mg/mL poly-D-lysine (Sigma-Aldrich) solution and incubated overnight at 37° C. The wells were washed three times with water and air-dried for at least 30 minutes. 120 µL of PA solution was pipetted evenly into the well and gelling solution comprised of 110 mM NaCl, 3 mM KCl, and 25 mM $CaCl_2$ was pipetted dropwise on top of the PA solution. The gels were incubated at 37° C. for 30 minutes, and then excess gelling solution was removed.

Cryogenic Transmission Electron Microscopy 300-mesh copper grids with lacey carbon film (Electron Microscopy Sciences) were glow discharged for 30 seconds in a PELCO easiGlow system (Ted Pella, Inc.). PA solutions were prepared as previously described and then diluted to 1 mM in water before imaging. 7 µL of PA solution was placed onto grids, blotted, and plunge-frozen in liquid ethane using an FEI Vitrobot Mark IV (FEI), maintained at 95-100% humidity. While submerged in liquid nitrogen, vitrified samples were transferred to a Gatan 626 cryo-holder (Gatan) and imaged on a JEOL 1230 TEM operating at 100 kV accelerating voltage. Liquid nitrogen temperatures were maintained during imaging, and micrographs were captured with a Gatan 832 CCD camera.

Conventional Transmission Electron Microscopy

PA solutions were diluted to 0.6 mM in water and immediately placed onto copper TEM mesh grids (Electron Microscopy Sciences) for 30 seconds, blotted twice with water, stained with 2% uranyl acetate, and air-dried for 15 minutes. Imaging was performed on an FEI Sprit G2 Transmission Electron Microscope.

Dynamic Light Scattering

DLS measurements were performed on a Malvern Zetasizer Nano ZSP light scattering spectrometer. The TGF-β1 mimetic peptide alone, without PA, was prepared at 1 wt % as previously described. During the sample measurement, the temperature was kept at 25° C. The sample was equilibrated for 30 seconds before each measurement was taken. The duration of each measurement was 10 seconds, and the measurement angle was 173° backscatter. The attenuator was determined by the instrument automatically, as was the number of accumulations for each run. Each measurement run was repeated 3 times.

X-Ray Scattering

Experiments were performed at beamline 5ID-D at the Dupont-Northwestern-Dow Collaborative Access Team Synchrotron Research Center at the Advanced Photon Source of Argonne National Laboratory. 4.8 mM PA solutions were prepared in quartz capillary cells and exposed to 17 keV monochromatic X-rays five times for 2-3 seconds. Scattering intensities were recorded on a CCD detector positioned 245 cm behind the samples. The collected two-dimensional scattering images were averaged by azimuthal integration using the data reduction program FIT2D, plotted against the wave vector $q=(4\pi)\sin(\theta/2)$, where $d=2\pi/q$. A 30 mM NaCl buffer-only sample was background-subtracted to obtain final intensities. SAXS patterns were plotted on a log-log scale and fit with a core-shell cylinder model when appropriate. WAXS patterns were plotted on a linear scale and peaks and minima in the data were identified using MATLAB peakfinder function.

Circular Dichroism

CD spectra were recorded on a JASCO model J-815 spectropolarimeter using a parallel plate quartz chamber of 0.5 mm optical length. PA solutions were diluted to 0.1 and 0.5 mM in water immediately before measurement. Spectra were collected over a wavelength range of 190-300 nm with a step size of 1 nm, scanning speed of 100 nm/minute, and standard sensitivity. High Tension voltage was recorded for each sample to ensure that the measurement was not saturated. An accumulation of 3 measurements was used and a 30 mM NaCl buffer-only sample was background-subtracted to obtain final spectra. All PA concentrations were analyzed together to ensure no linear dichroism, and spectra of 0.5 mM PA solutions were used for final analysis.

Fourier Transform Infrared Spectroscopy

PA solutions were prepared in water-free conditions using previously described methods. PAs were solubilized in $D_2O$, pH adjusted with DOH, and diluted to 12 mM PA and 30 mM NaCl using 150 mM NaCl in $D_2O$. PA solutions were diluted to 5 mM in $D_2O$ immediately before measurement, and then placed between two $CaF_2$ windows with a 50 µm separation. Transmittance was measured on a Bruker Tensor 37 FTIR Spectrometer. Spectra were recorded and averaged over 25 scans with a resolution of 1 $cm^{-1}$ and a 30 mM NaCl in $D_2O$ buffer-only sample and air were background-subtracted to obtain final spectra. Peaks in the spectra were identified using MATLAB peakfinder function and secondary structures were identified through peak positions.

Fluorescence Anisotropy

PA co-assemblies of diluent PA, TGF-β1 mimetic PA, and fluorescent dye-conjugated TGF-β1 mimetic PA were prepared in a 90:8:2 mol % ratio. The dye-conjugated PA was synthesized as previously described with a tetramethylrhodamine (TAMRA) molecule conjugated to the N-terminal amine of the TGF-β1 mimetic epitope. The PA solutions were prepared as previously described and diluted immediately before measurement to 100 µM PA, 100 µM $CaCl_2$), and 30 mM NaCl. Fluorescence measurements were performed on an ISS PC1 photon counting steady-state fluorescence spectrometer equipped with a 300 W xenon arc lamp with power set to 18 A. Excitation slit widths of 1 mm (8 nm bandwidth) and emission slit widths of 0.5 mm (4 nm bandwidth) were used. Fluorescence anisotropy measurements were performed with $\lambda ex=554$ nm and $\lambda em=580$ nm according to the equation:

$$A = \frac{F_{\parallel} - gF_{\perp}}{F_{\parallel} + 2gF_{\perp}}$$

Where $F_{\parallel}$ is the intensity parallel to the excitation plane, $F_{\perp}$ is the intensity perpendicular to the excitation plane, and g is the g-factor, which accounts for differences in emissions between the perpendicular and parallel gratings.[1] Measurements were taken in triplicate and averaged for final data analysis.

Transverse-Relaxation Nuclear Magnetic Resonance Spectroscopy

NMR spectra were acquired at 600 MHz on a Brucker Neo system with QCI-F cryoprobe. NMR spectra for PAs were recorded at 25° C. using TFA-d, $H_2O/D_2O$ in 9/1 ratio ($D_2O$ contains 0.05 wt. % 3-(trimethylsilyl) propionic-2,2, 3,3-$d_4$ acid, sodium salt) as solvents. Chemical shifts are reported in part per million (ppm). The 900 pulse width was 15 μs and typical spectra required 32 scans.

The spin-spin relaxation rates were measured using the Carr-Purcell-Gill-Meiboom pulse sequence with a delay time of 0.2 ms in a variable loop. The peak intensity data was fit to and exponential in the form:

$$I = I_0 e^{-(R_2 \tau)}$$

where τ is the length of the delay time, R2 is the spin-spin relaxation rate and b are the baseline.[2]

Cell Culture

C28/I2 human articular chondrocytes (Millipore) were maintained using standard cell culture techniques in DMEM High Glucose Medium (Gibco) supplemented with 10% fetal bovine serum (Denville Scientific), 100 U/mL penicillin, and 100 μg/mL streptomycin (Gibco). Cells were passaged using 0.25% trypsin (Gibco) and used for experiments at passages 3-8.

PA Cell Treatment In Vitro

PA solutions (backbone PA, TGF PA, ln TGF PA, and peptide only) were prepared at 1 wt % as previously described, under sterile conditions. For cell treatments lasting <24 h, PA treatment solutions or native rhTGF-β1 protein (R&D Systems) were diluted in starvation medium, which comprised of DMEM High Glucose Medium (Gibco) supplemented with 0.5% fetal bovine serum (Denville Scientific), 100 U/mL penicillin, and 100 μg/mL streptomycin (Gibco). For cell treatments lasting 24 h or more, PA treatment solutions or native rhTGF-β1 protein (R&D Systems) were diluted in complete growth medium. PA solutions were prepared at a range of concentrations, 1, 10, 50, and 100 μM, where the concentration refers to the concentration of the epitope PA.

For cell viability assays, cells were seeded in 48-well plates at a density of approximately 15,400 cells/well and cultured for 24 h. Cells were then treated with PA in solution for 24 h or 3 days in vitro.

For western blot of 4 h PA treatments, cells were seeded in 6-well plates at a density of 600,000 cells/well and cultured for 24 h. Cells were then serum-starved for 20 h in DMEM High Glucose Medium (Gibco) supplemented with 0.5% fetal bovine serum (Denville Scientific), 100 U/mL penicillin, and 100 μg/mL streptomycin (Gibco). Cells were then treated with PA in solution for 4 h in vitro. For western blot of 3-day PA treatments, cells were seeded in 6-well plates at a density of 230,000 cells/well and cultured for 24 h. Cells were then treated with PA in solution for 3 days in vitro.

For immunocytochemistry (ICC), 12-mm glass coverslips were coated with sterile filtered 0.01 mg/mL poly-D-lysine (Sigma-Aldrich) solution and incubated overnight at 37° C. The coverslips were washed three times with sterile water and air-dried for at least 30 minutes. Cells were seeded on coverslips at a density of approximately 3,000 cells/coverslip and cultured for 24 h. Cells were then treated with PA in solution for 3 days in vitro. Following treatment, cells were fixed in 4% paraformaldehyde for 15 minutes at room temperature.

Viability Assays

For 2D viability assays, cells were cultured and treated with PA solutions in vitro as previously described. After 24 h or 3 days of culture, cells were washed with HBSS (Gibco), and media was exchanged with HBSS containing 2 μM Calcein AM (Invitrogen) and 100 ng/mL propidium iodide (Sigma-Aldrich) for 30 minutes at 37° C. Cells were washed with HBSS and imaged.

For 3D viability assays, cells were encapsulated in PA gels and cultured in vitro as described below. After 3 days of culture, a fraction of the media was collected to measure the presence of lactate dehydrogenase (LDH), a cytosolic enzyme only released upon cell lysis, using CyQUANT™ LDH Cytotoxicity Assay (Invitrogen).

Western Blot

Protein was extracted from cells using Halt Protease and Phosphatase Inhibitor Cocktail (Thermo Scientific) and a BCA assay (Thermo Scientific) was performed to determine protein content of each sample. Cell protein was loaded into and separated using a 4-20% SDS-PAGE gel (Bio-Rad). It was then electrotransferred from the gel to a nitrocellulose membrane (Bio-Rad). The membranes were blocked with 10% milk solution (Bio-Rad) for 30 minutes followed by an overnight incubation with primary antibodies at 4° C. The following primary antibodies were used: rabbit anti-pSmad2 (1:1000, Cell Signaling), rabbit anti-Smad2 (1:1000, Cell Signaling), rabbit anti-Sox9 (1:500, Abcam), mouse anti-Aggrecan (1:500, ThermoFisher), rabbit anti-COMP/Cartilage oligomeric matrix protein (1:500, Abcam), mouse anti-Collagen II (1:500, ThermoFisher), and mouse anti-Actin (1:1000, Novus Bio). Membranes were then incubated with their corresponding secondary HRP-conjugated antibodies (1:1000, ThermoFisher). Protein signals were detected using Radiance Bioluminescent ECL substrate (Azure Biosystems). Densitometry analysis, standardized to total receptor content or actin as a control for protein loading, was performed using ImageJ software. For quantification, experimental triplicate samples were analyzed, and two different experiments were conducted.

Immunocytochemistry

Fixed samples were permeabilized and blocked in a solution of 0.1% (v/v) Triton X-100 and 1% normal horse serum (Invitrogen) for 2 hours at room temperature. Samples were incubated with primary antibodies overnight at 4° C. The following primary antibodies were used: rabbit anti-Sox9 (1:500, Abcam), mouse anti-Aggrecan (1:500, ThermoFisher), mouse anti-Collagen II (1:500, ThermoFisher), and mouse anti-Nuclei (1:500, Sigma-Aldrich). The next day, samples were incubated with AlexaFluor 488 secondary antibody, AlexaFluor 555 secondary antibody, Phalloidin AlexaFluor 488, and/or Phalloidin AlexaFluor 633 (1:1000, Invitrogen) for 2-3 h at room temperature. For 2D cell culture, samples were then incubated with DAPI (1:1000, Invitrogen) for 10 minutes at room temperature. If not already on a glass coverslip, samples were mounted with Immu-Mount (Thermo Scientific) and imaged on a Nikon A1R Spectral microscope. Image analysis was performed using ImageJ software.

Cellular Encapsulation

Chondrocytes were trypsinized and resuspended in growth media for counting, and then pelleted and resuspended to $6 \times 10^7$ cells/mL in growth media. The cell solution was mixed 1:2 v/v with sterile PA solution prepared at 3 wt % in 30 mM NaCl. For gels also encapsulating rhTGF-β1 protein (R&D Systems), soluble protein was added to PA solutions after thermal annealing. 120 μL of PA/cell solution was mixed thoroughly by pipetting gently and then placed into PDL-coated 12-well chamber slides (Ibidi). Sterile gelling solution, comprised of 110 mM NaCl, 3 mM KCl, and 25 mM CaCl₂, was pipetted dropwise on top of the PA/cell solution and the gels were incubated for 30 minutes at 37° C. Following incubation, excess gelling solution was removed and 250 μL of growth media was added to each well. The media was removed after 3 days for LDH viability assays as described above. For ICC, after 3 days of in vitro culture, gels were fixed in 4% paraformaldehyde for 30 minutes at room temperature.

Statistical Analysis

Statistical analysis was performed using MATLAB 2021 software. Analysis of variance (ANOVA) tests of significance with Tukey's post-hoc analysis was used for all multiple group analyses, except for cell area analysis, in which the data were non-Gaussian and Kruskal-Wallis test was used instead. Error bars represent standard error of mean.

Results

Design of TGF-β1 Mimetic PA Nanostructures

Figure 1A:
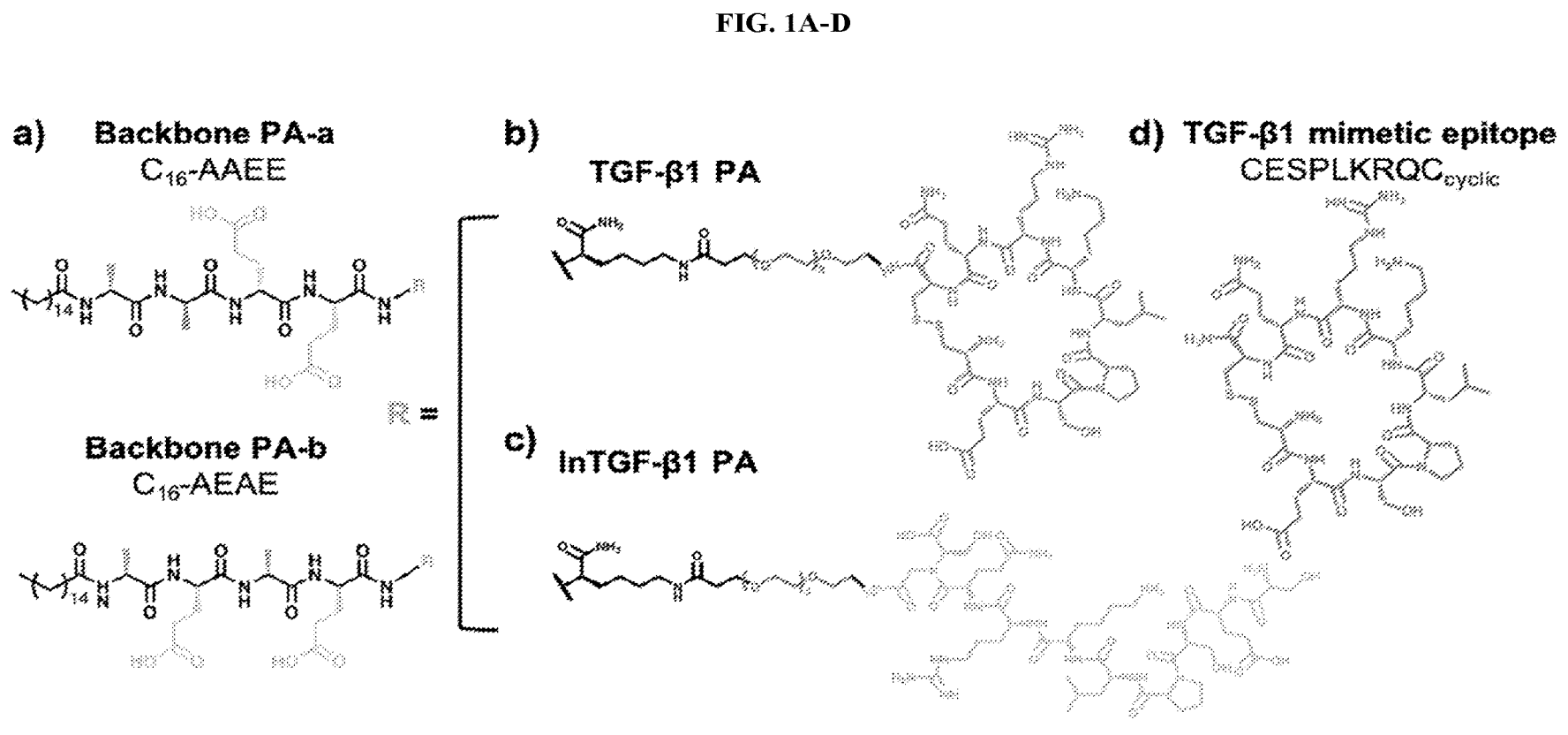

Experiments were conducted during development of embodiments herein to develop supramolecular nanostructures that mimic TGF-β1 signaling in cartilage through the display of the cyclic peptide CESPLKRQC (SEQ ID NO: 1). A TGF-β1 mimetic PA molecule (TGF PA) was designed by conjugating this peptide to the C-terminus of two different PA molecules through a tetra(ethylene glycol) spacer (FIG. 1). A linear, non-cyclized derivative of the mimetic PA (ln TGF PA) presenting the epitope SESPLKRQS (SEQ ID NO: 2) was also designed. PA assemblies containing 100 mol % of the epitope PA molecules were unable to form long fibrous structures likely due to steric demands of the epitopes (FIG. 7). Each backbone PA alone forms robust high-aspect-ratio structures,[37] which have been shown to be more conducive to cell viability and bioactivity.[38,39] Thus, the non-bioactive diluent backbone PA molecules (Backbone PA-a and Backbone PA-b) were co-assembled each with their respective PA conjugated to the cyclic epitope (TGF PA-a and TGF PA-b) or the non-cyclized control (ln TGF PA-a and ln TGF PA-b) to form long fibrous nanostructures displaying the epitopes on their surfaces. To examine whether epitope bioactivity is enhanced by its presentation on the PA supramolecular nanostructures, the soluble cyclic TGF-β1 mimetic peptide was also evaluated alone.

Materials Characterization of TGF-β1 Mimetic PA Nanostructures

Figure 8:
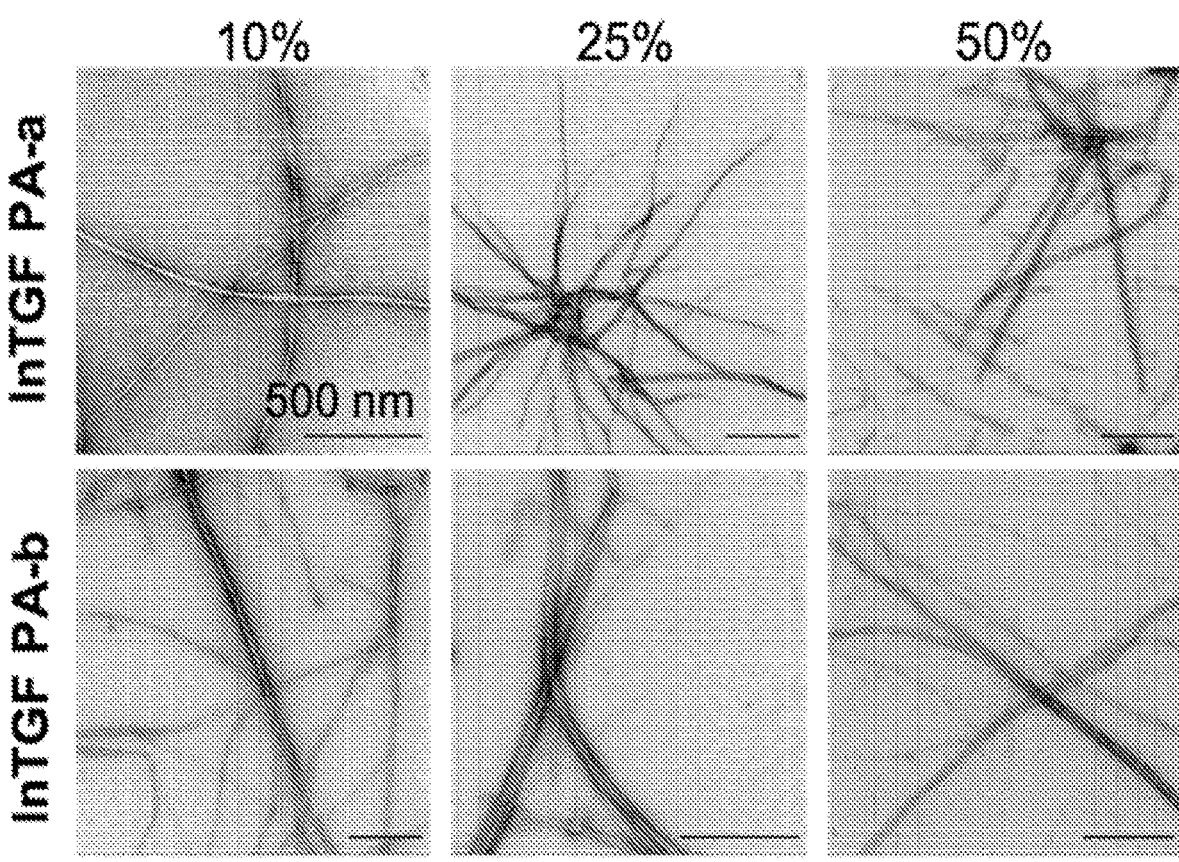
FIG. 8: Cryo-TEM micrographs of linear ln TGF PA-a (top) and ln TGF PA-b (bottom) co-assembled with diluent Backbone PA-a and Backbone PA-b, respectively, at 10, 25, and 50 mol %.
Figure 9:
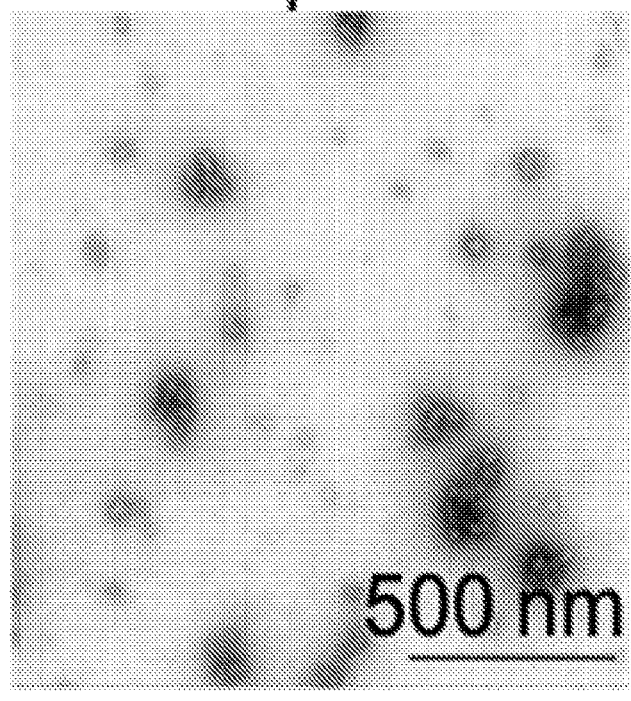
FIG. 9: Cryo-TEM micrograph of TGF mimetic peptide at 100 mol %. (b) Dynamic light scattering of micellar TGF mimetic peptide aggregates at 100 mol %.
Figure 10:
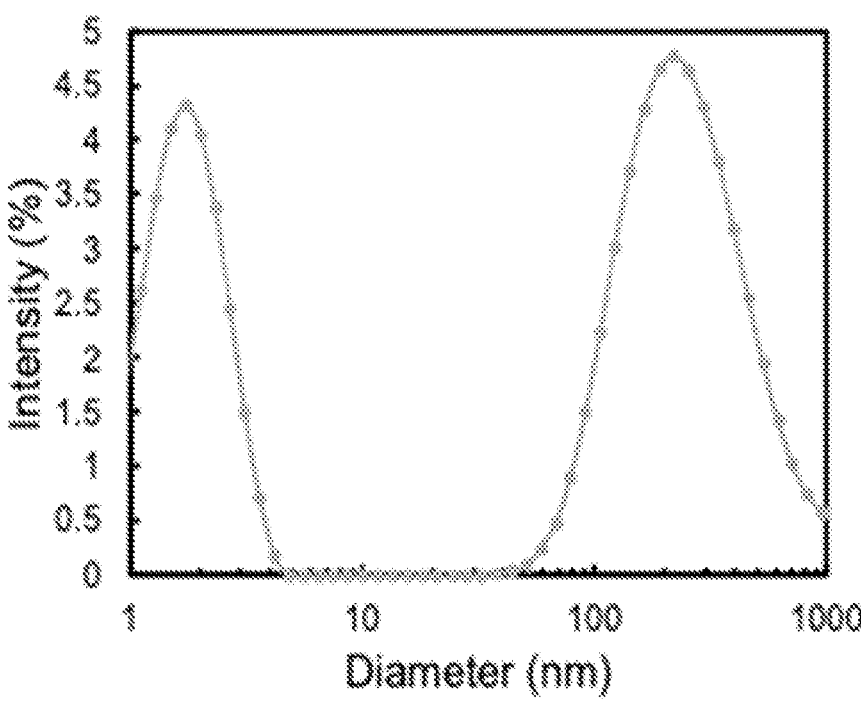
FIG. 10: Dynamic light scattering of micellar TGF mimetic peptide aggregates at 100 mol %.
Figure 11:
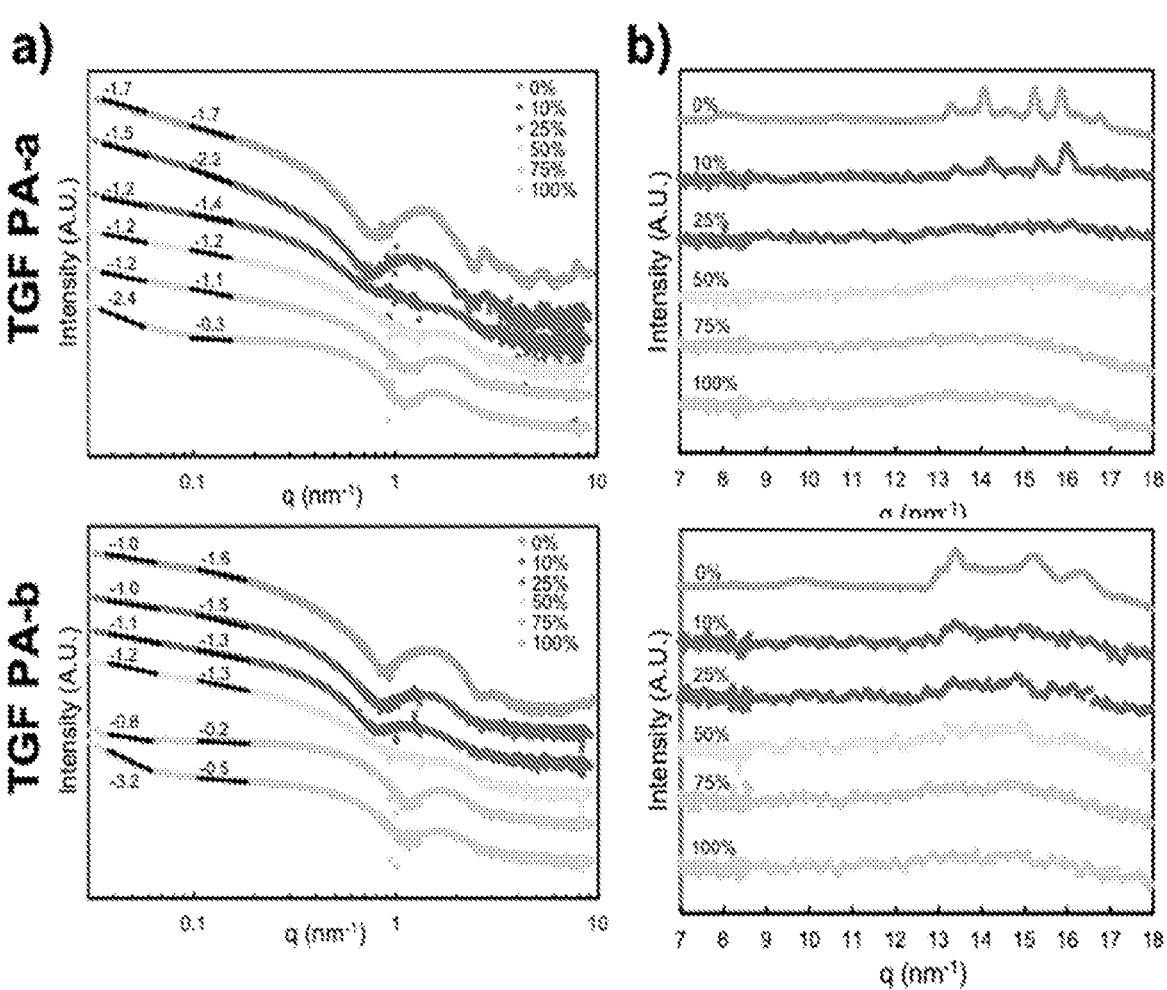
FIG. 11A-B: Structural analysis of TGF PA-a (top) and TGF PA-b (bottom) co-assembled with diluent Backbone PA-a and Backbone PA-b, respectively, at 10, 25, 50, 75, and 100 mol %. (a) SAXS patterns and (b) WAXS patterns of TGF PA co-assemblies.
Figure 12:
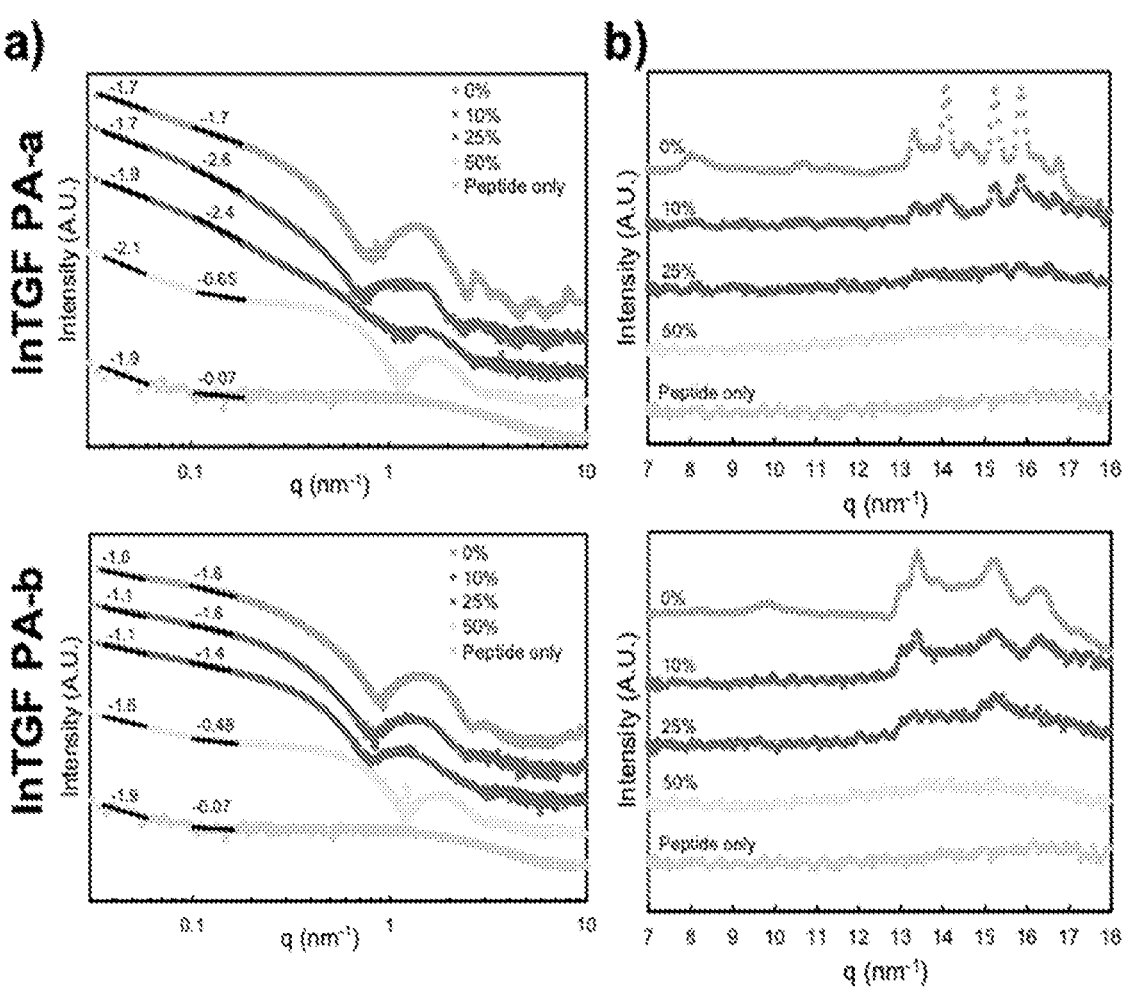
FIG. 12A-B: Structural analysis of linear ln TGF PA-a (top) and ln TGF PA-b (bottom) co-assembled with diluent Backbone PA-a and Backbone PA-b, respectively, at 10, 25, and 50 mol %. (a) SAXS patterns and (b) WAXS patterns of ln TGF PA co-assemblies and peptide micellar structures.
Figure 13:
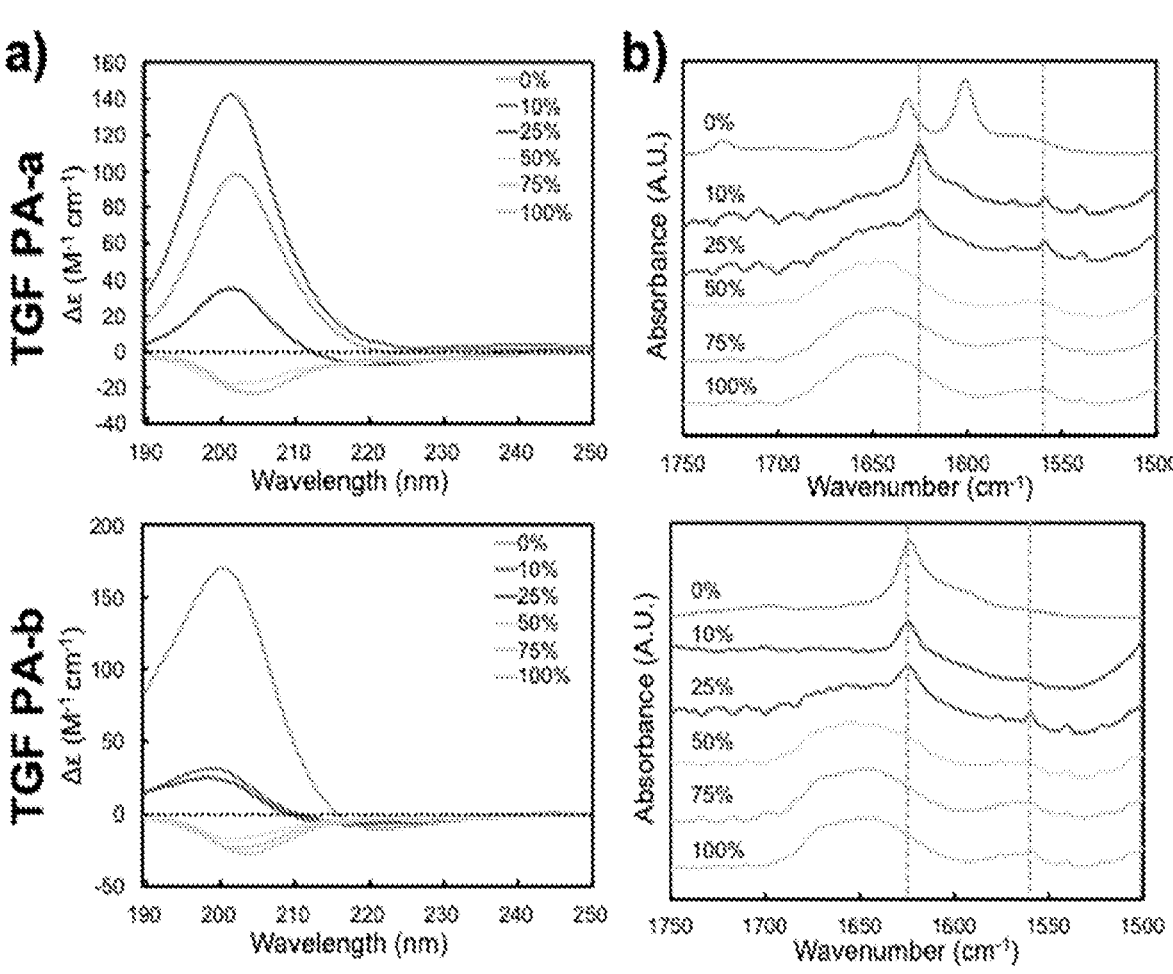
FIG. 13A-B: Secondary structure analysis of TGF PA-a (top) and TGF PA-b (bottom) co-assembled with diluent Backbone PA-a and Backbone PA-b, respectively, at 10, 25, 50, 75, and 100 mol %. (a) Circular dichroism and (b) FTIR spectra of TGF PA co-assemblies.
Figure 14:
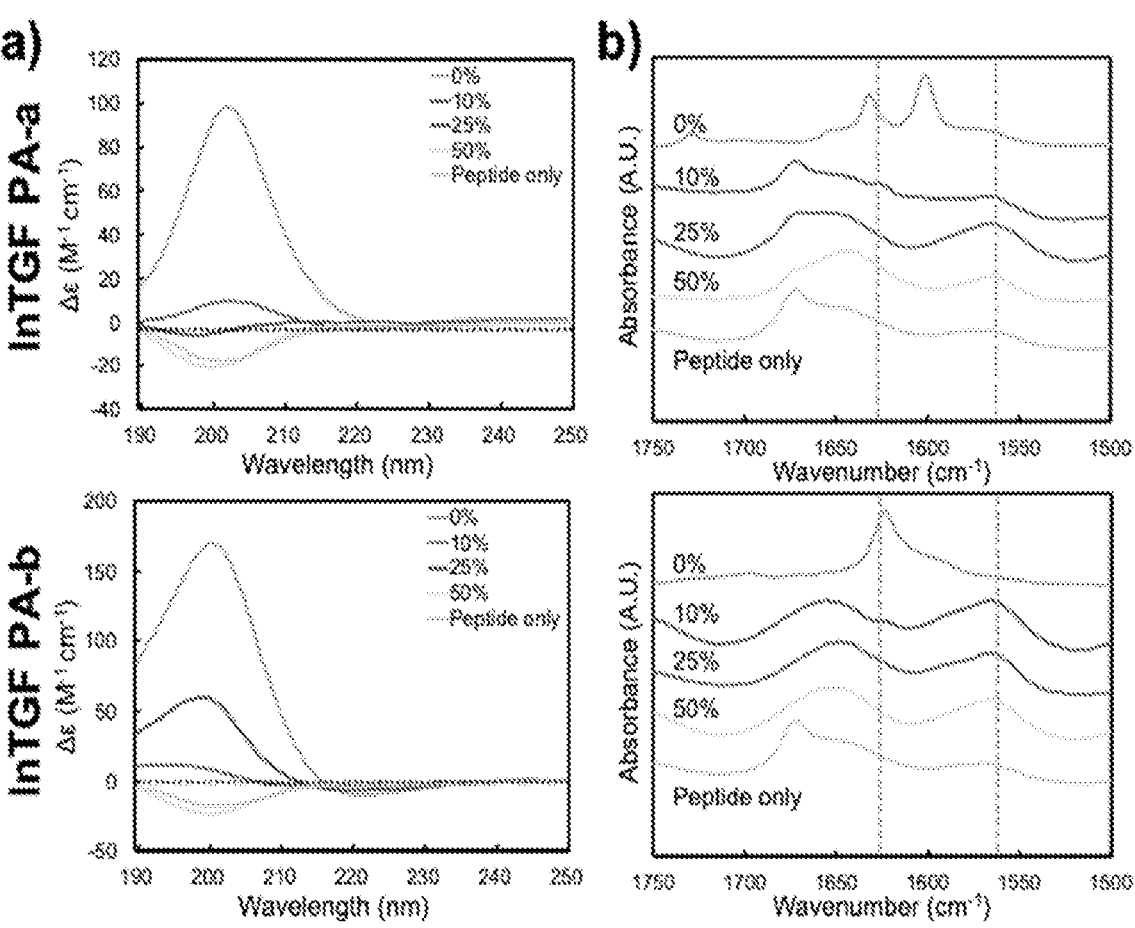
FIG. 14A-B: Structural analysis of linear ln TGF PA-a (top) and ln TGF PA-b (bottom) co-assembled with diluent Backbone PA-a and Backbone PA-b, respectively, at 10, 25, and 50 mol %. (a) Circular dichroism and (b) FTIR spectra of ln TGF PA co-assemblies and peptide micellar structures.

Since the molar ratio of bioactive and diluent PA has been shown to affect nanostructure morphology, epitope presentation, and bioactivity,[28,30,31] various co-assembly ratios (10, 25, 50, 75, and 100 mol %) of the epitope PA with the corresponding diluent backbone PA were characterized to determine the optimal ratio for self-assembly into long, uniform structures that promote cell viability and bioactivity. Cryogenic transmission electron microscopy (cryo-TEM) revealed clear differences in nanostructure morphology between the different backbone systems and co-assembly ratios (FIGS. 2a-f, FIG. 7, and FIG. 8). The diluent backbone PA alone formed high-aspect-ratio twisted ribbon-like structures (FIGS. 2a and 2d), which changed upon co-assembly with the epitope PA molecules. At a molar ratio of 10%, both TGF PA systems and ln TGF PA systems formed high-aspect-ratio structures. TGF PA-a formed wide helical ribbon-like structures 50-60 nm in width and TGF PA-b formed one-dimensional cylindrical fibers (FIGS. 2b and 2e). As the molar ratio of TGF PA increased to 50 mol % or higher, both systems formed short, fibers or micelles, likely due to steric repulsion from the cyclic epitopes (FIG. 7). Both linear ln TGF PA systems formed narrow twisted ribbons 20-30 nm width at 10 mol % (FIGS. 2c, 2f, and 8). Dynamic light scattering revealed the TGF-β1 mimetic epitope alone formed micelles with a hydrodynamic diameter of approximately 2 nm and aggregates of micelles on the order of 200 nm (FIGS. 9 and 10).

To characterize these morphologies observed in cryo-TEM more quantitatively, the nanostructures were analyzed in situ using small- and wide-angle x-ray scattering (SAXS and WAXS) (FIGS. 2g-h, 11, 12). The SAXS intensity profiles plotted on a log-log scale could be fit linearly in the low-q Guinier region with a slope of approximately −2 for TGF PA-a and −1 for TGF PA-b, indicating high-aspect-ratio two-dimensional and one-dimensional structures, respectively (FIG. 2g).[40] WAXS revealed distinct differences in the molecular packing schemes between the two backbone systems (FIG. 2h). The multiple sharp peaks in TGF PA-a WAXS patterns indicated highly ordered crystalline packing, contrasting with the less ordered internal organization of TGF PA-b. Next, to investigate the secondary structure of the assemblies and the degree of hydrogen bonding among the PA molecules, circular dichroism (CD) and Fourier-transform infrared (FTIR) spectroscopy were performed (FIGS. 2i-j, 13, and 14). Backbone PA-a, Backbone PA-b, and TGF PA-a assemblies showed strong β-sheet-like character with CD maxima around 195 nm,[41] but while both ln TGF PA assemblies had little to no β-sheet structure (FIG. 2i), indicating that the linear epitopes more severely frustrated hydrogen bonding required for β-sheet formation. Similarly, FTIR spectra of both TGF PA-a and TGF PA-b assemblies displayed the canonical β-sheet amide I band around 1625-1640 cm⁻¹,[42] which was absent in both ln TGF PA spectra (FIG. 2j). Backbone PA-a also displayed a second peak around 1600 cm⁻¹ which was absent from all other samples (FIG. 2j). Different combinations of backbone PA and epitope PA led to changes in internal order and secondary structure of the assemblies.

Figure 15:
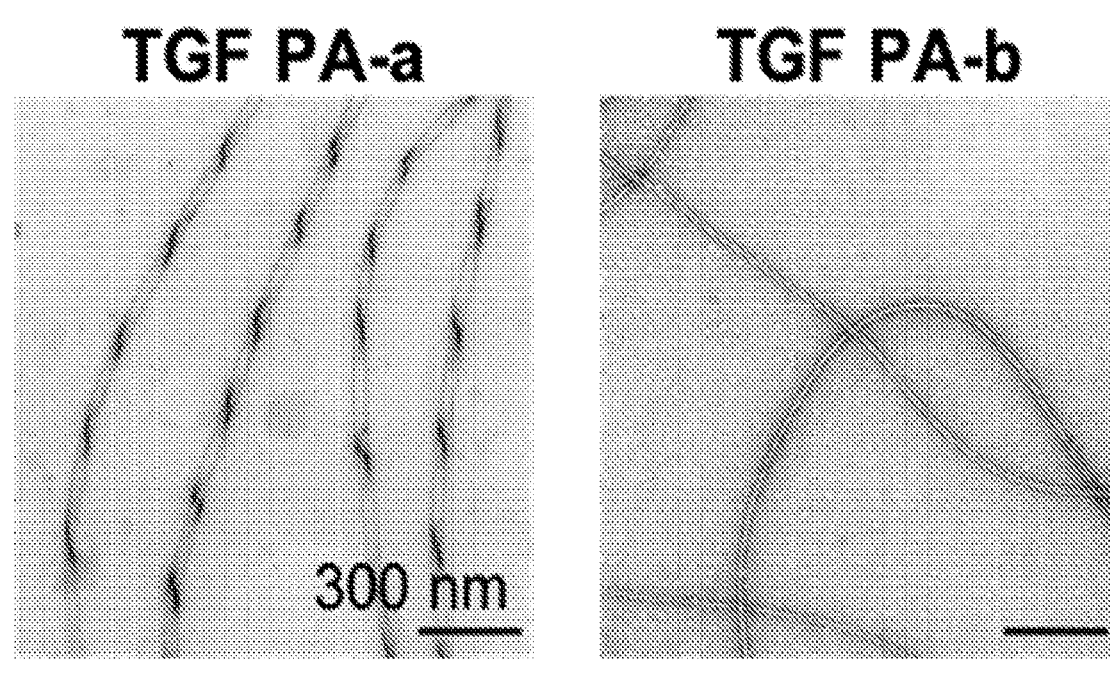
FIG. 15: TEM micrographs of TGF PA nanostructures where 0.2 mol % of TGF PA molecules are conjugated to TAMRA dye, and TGF PA is co-assembled at 10 mol % with diluent backbone PA.

To further probe the intermolecular dynamics and mobility of individual PA molecules within the assemblies, fluorescence anisotropy (FA) was used to measure the rotational diffusion of TAMRA-labeled epitopes within the TGF PA nanostructures (FIG. 3a). The TGF PA was co-assembled at 10 mol % with diluent backbone PA and 0.2 mol % of the TGF PA molecules were conjugated with TAMRA on the cyclic epitope. It was confirmed that the TAMRA fluorophore did not interfere with self-assembly and that the PA nanostructures with TAMRA-labeled epitopes formed the same morphologies as the unlabeled assemblies (FIG. 15). FA revealed significantly lower anisotropy values in TGF PA-a, which indicated increased epitope mobility, in terms of rotational diffusion, compared to TGF PA-b (FIG. 3a). This higher rotational diffusion may allow the epitopes on TGF PA-a assemblies to change conformation or extend from the nanostructure and bind with cell receptors.

To better understand the internal dynamics of the assemblies and translational diffusion of individual PA molecules, transverse-relaxation nuclear magnetic resonance (T2-NMR) spectroscopy was used to measure the spin-lattice relaxation (T2) rates of the methylene protons on the E carbon (HE) of the lysine residue in the CESPLKRQC (SEQ ID NO: 1) cyclic epitope (observed at 2.64 ppm) and the methyl protons on the terminal carbon of the alkyl tail of the peptide N-terminus (0.77 ppm) (FIGS. 3b-c, 16, and 17). In contrast to FA which measures only the rotational diffusion of the labeled epitopes, T2-NMR can also probe the translational diffusion of PA molecules within the assemblies and estimate intermolecular cohesion. The relaxation rate for the alkyl tail protons in TGF PA-a assemblies was much higher, nearly five times higher, than that of TGF PA-b assemblies (FIGS. 3b-c). This high relaxation rate was consistent with lower translational diffusion and stronger intermolecular cohesion, as described by the attractive forces between PA molecules that stabilize the supramolecular structures. The T2-NMR measurements from the alkyl tail protons confirmed our WAXS results, indicating that TGF PA-a assemblies had high internal order and stronger intermolecular cohesion compared to TGF PA-b. In great contrast, the epitope protons in both TGF PA-a and TGF PA-b assemblies had similar low relaxation rates (FIGS. 3b-c). This indicated that although TGF PA-a assemblies had high internal order, the epitopes presented on the nanostructure surfaces were flexible and mobile. This coexistence of internal crystallinity and epitope mobility revealed that the epitope PA molecules significantly impacted the supramolecular dynamics within the TGF PA-a nanostructures. In TGF PA-a assemblies, the cyclic epitope PA molecules may have created local disruptions in the crystal structure, affording the epitopes more mobility. Similar T2-NMR measurements of the alkyl tail protons in backbone PA assemblies revealed increased supramolecular dynamics in the outer periphery of Backbone PA-a assemblies compared to Backbone PA-b (Table 1). These reciprocal effects of backbone and epitope PA dynamics in TGF PA-a were unexpected because they showed that even when the inner core of an assembly is highly ordered and cohesive, the epitope and outer periphery can still exhibit dynamic mobility. TGF PA-a nanostructures also had increased surface area due to their wide belt-like morphology, which likely presents the cyclic epitope molecules with dynamic range of motion to interact with cells more favorably.

TABLE 1

| ¹H spin-lattice relaxation rates of protons in Backbone PA-a and Backbone PA-b. | |
| --- | --- |
| | Methyl proton of terminal carbon of alkyl chain |
| Backbone PA-a | 3.67 ± 0.23 s⁻¹ |
| Backbone PA-b | 20.49 ± 0.58 s⁻¹ |

Cellular Responses to the TGF-β1 Mimetic Peptide Amphiphile Nanostructures

Figure 18A:
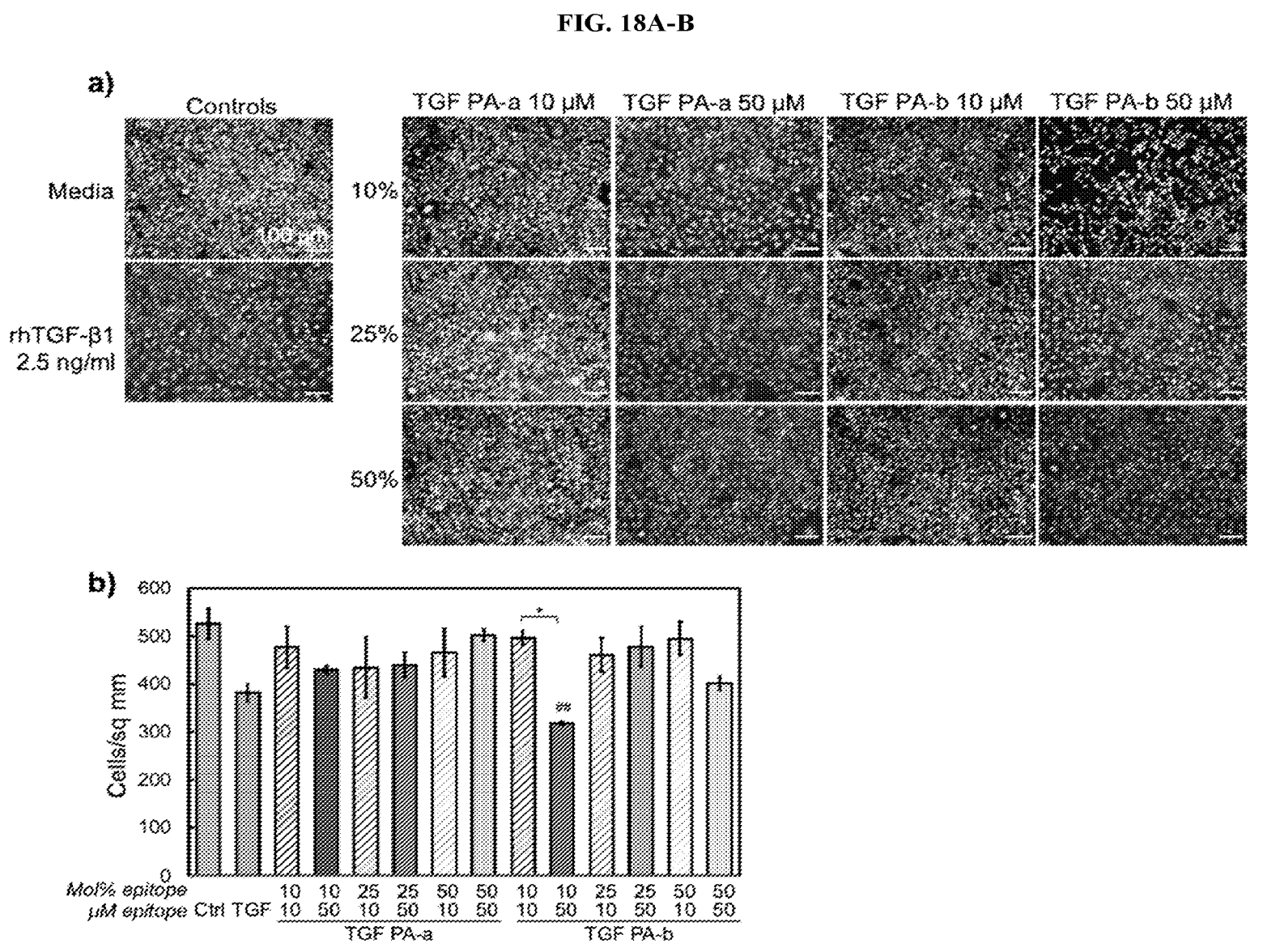
Figure 19A:
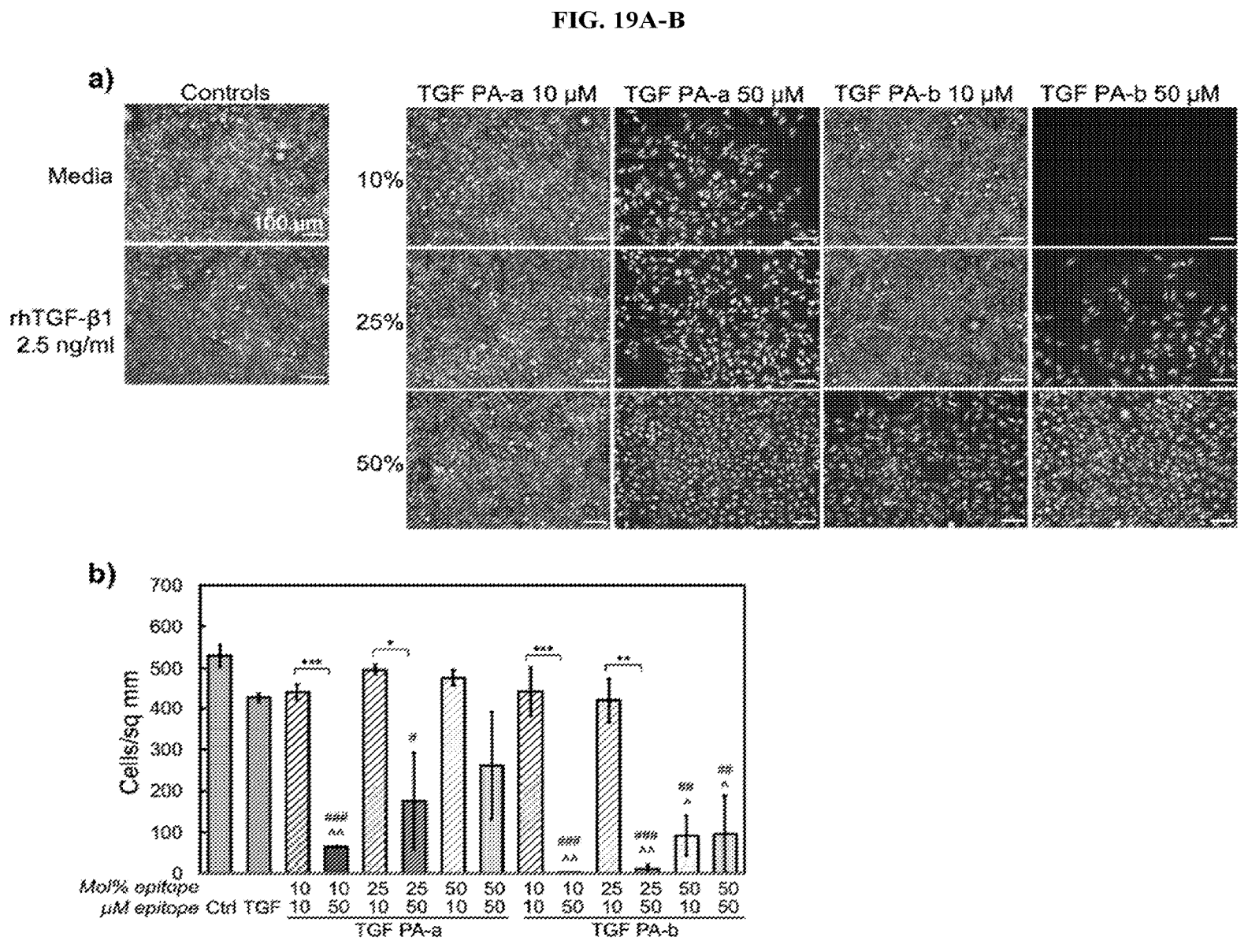

Considering differences in morphology, internal order, and supramolecular dynamics between the TGF PA-a and TGF PA-b nanostructures, the effects of these differences on bioactivity were analyzed by treating human articular chondrocytes in vitro with PA solution diluted in media. The biocompatibility was measured by treating cells with each TGF PA solution at different co-assembly ratios and concentrations, and then analyzed viability after 24 h and three days in culture (FIGS. 18 and 19). After 24 h, all PA treatments showed high viability (>300 cells/mm²) at both 10 μM and 50 μM. After three days, nearly all 10 μM PA treatments showed high viability (>400 cells/mm²) as well. The 25 mol % and 50 mol % co-assemblies varied in both biocompatibility and morphology, but the 10% co-assemblies that formed uniform fibrous structures revealed consistent concentration and time-dependent biocompatibility. The total PA concentrations were altered in co-assemblies of 10 mol % epitope to determine the optimal concentrations for biocompatibility. The cells were treated in solution with each TGF PA, ln TGF PA, backbone PA, peptide alone, or native recombinant human TGF-β1 (rhTGF-β1), at a range of concentrations (FIGS. 20 and 21). After 24 h in culture, all PA treatments, except Backbone PA-b and ln TGF PA-b at 100 μM, showed high viability (>300 cells/mm²). After three days in culture, all PA treatments at or below 10 μM showed high viability (>300 cells/mm²), while higher concentrations gave significant decreases in viability, possibly due to over-signaling or excess PA material that accumulated on top of cells after three days. These results informed experimental design that 50 μM and 10 μM PA treatments were appropriate concentrations for treatment timepoints up to 24 h and three days, respectively.

The Backbone PA-a systems, TGF PA-a and ln TGF PA-a, showed higher biocompatibility than the corresponding Backbone PA-b systems after three days. This difference in biocompatibility was unexpected because all the assemblies formed long high-aspect-ratio structures, a physical attribute generally attributed to greater cell viability.[35,43] The molecules in each system differed only in the order of two adjacent amino acids within the non-bioactive PA backbone. However, WAXS and T2-NMR spectroscopy revealed less internal order and lower relaxation rates for TGF PA-b assemblies, suggesting increased translational diffusion and weaker internal cohesion that may have caused them to disrupt cell lipid membranes via the disassociation of TGF PA-b molecules from the nanofibers, resulting in cell death. Conversely, the high internal order and relaxation rates for TGF PA-a assemblies indicated stronger internal cohesion that allowed the high-aspect-ratio nanostructures to remain intact and coexist and interact with cells.

TGF-β1 Mimetic PA Nanostructures Activate Intracellular Signaling

Figure 22:
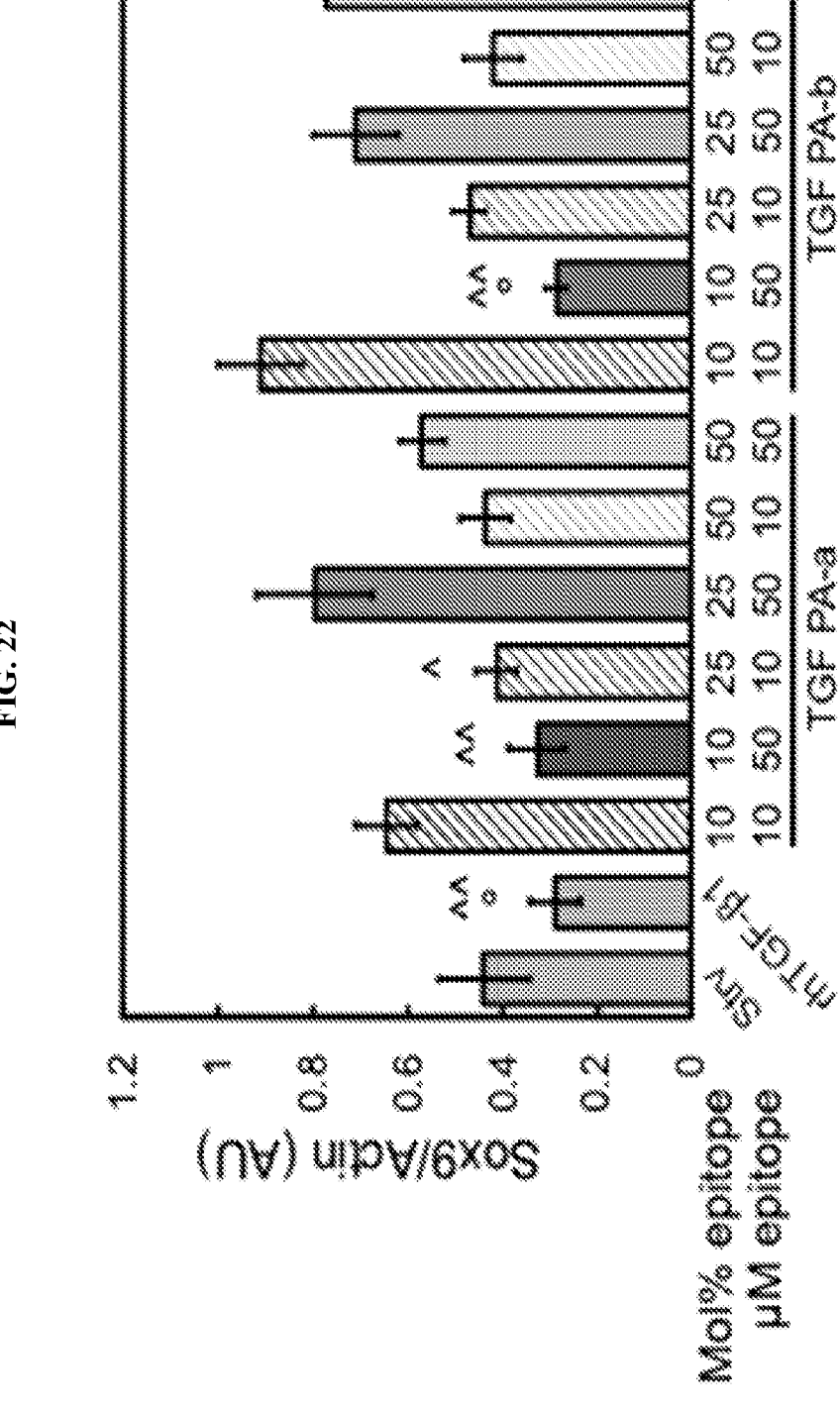
FIG. 22: Quantitative densitometry analysis of western blot data from FIG. 4*a* showing Sox9 expression normalized to actin (^, vs 10% TGF PA-b 10 PM; °, vs 25% TGF PA-b 50 μM). (°/^, $p<0.05$; ^^, $p<0.01$).

Experiments were conducted during development of embodiments herein to assess the ability of the PA materials to activate intracellular TGF-β1 signaling in chondrocytes. It was hypothesized that for TGF PA-a nanostructures, the wide belt-like morphology, crystalline internal order, and dynamic epitopes would contribute to enhanced bioactivity for chondrogenic signaling. A co-assembly and concentration sweep was performed by treating cells with each TGF PA at different co-assembly ratios (10, 25, and 50 mol %) and concentrations (10 and 50 μM), rhTGF-β1 as a positive control, or starvation media as a negative control. After 4 h of treatment, western blot analysis was performed to assess levels of phosphorylated Smad2 (p-Smad2) and Sox9 (FIGS. 4a-b and 22). Smad2 phosphorylation is the first step in canonical TGF-β1 signaling in cartilage following receptor binding. Upon activation, phosphorylated Smad2 and Smad3 form a complex with Smad4, which translocates to the nucleus to initiate transcription, including that of chondrogenic genes.[11,12] TGF PA-a at 10 mol % co-assembly and 50 μM showed strong p-Smad2 activation. Again, higher co-assembly ratios induced little cellular response, likely because the short fibers and micelles displayed the epitopes in less favorable conformations or distributions, preventing the enhanced signaling seen previously from long fibrous structures. Sox9 is a nuclear transcription factor expressed during early mesenchymal stem cell condensation, and was not expected to be significantly upregulated in mature chondrocytes.[10] While there was no significant upregulation of Sox9, all conditions showed baseline levels of expression, indicating healthy chondrocyte phenotype (FIG. 22).

Based on the biocompatibility and bioactivity results, experiments were conducted with 10 mol % co-assemblies for all epitope PA assemblies, 50 μM for short (<24 h) treatments, and 10 μM for long (>24 h) treatments. The cells were treated with 50 μM each TGF PA, ln TGF PA, backbone PA, peptide alone, or rhTGF-β1 for 4 h. Western blot analysis showed no activation by the backbone PA, linear epitope PA, or peptide alone, confirming the hypotheses that both the cyclization of the epitope and its presentation on the PA nanostructure conferred bioactivity (FIGS. 4c-d). TGF PA-a upregulated p-Smad2 significantly more than all other PA treatments, including its constitutional isomer, TGF PA-b. This further supported the hypothesis that the inner PA backbone affects bioactive signaling through morphology and internal dynamics, enhancing cell receptor interaction with epitopes presented more favorably on TGF PA-a assemblies. Next, to study the nature of the TGF-β1 activation by mimetic PA nanostructures, cells were treated with TGF PA-a, TGF PA-b, or rhTGF-β1, each with or without the addition of pan-TGF-β-neutralizing antibody, 1D11, which has been shown to neutralize all three isoforms of TGF-β in vitro and in vivo.[44-46] Western blot analysis revealed that 1D1 effectively neutralized TGF PA-a, TGF PA-b, and rhTGF-β1 in their activation of p-Smad2 (FIGS. 4e-f). Comparing the activation of p-Smad2 with and without 1D11, the neutralizing effect of 1D11 on TGF PA-a was statistically significant whereas its effect on TGF PA-b was not, most likely because TGF PA-a upregulated p-Smad2 more than TGF PA-b. These results confirmed that the mimetic TGF PA-a nanostructures activated intracellular TGF-β1 signaling in chondrocytes.

TGF PA Nanostructures Enhance ECM Synthesis in Chondrocytes

Since the primary role of chondrocytes in articular cartilage is maintenance of the ECM,[1,8] the synthesis of cartilaginous proteins was analyzed after 10 μM PA treatment for three days in vitro. Using western blot, levels of collagen II (Col2a1), cartilage oligomeric matrix protein (COMP), and aggrecan (Acan), all essential components of articular cartilage,[10,12] and transcription factor Sox9 (FIGS. 5a-b) were analyzed. Generally, TGF PA-a upregulated ECM synthesis significantly more than all other PA treatments. The backbone PA, linearized epitope PA, and peptide alone treatments again showed low activation, further demonstrating that the presentation of the cyclic epitope on the PA nanostructure was critical for bioactivity. Interestingly, cells treated with TGF PA-a had significantly higher levels of collagen II than those treated with native rhTGF-β1 protein. Chondrocyte signaling is largely mediated by physical cell-ECM interactions, such as integrin-collagen II binding[47] and mechanical activation of ECM-sequestered endogenous TGF-β1,[48] indicating that the morphology and supramolecular dynamics of the TGF PA-a nanostructures may have physically presented the mimetic epitopes more favorably for receptor binding.

To confirm these results from western blot, immunocytochemistry (ICC) staining and fluorescence intensity image analysis was performed on cells treated under the same conditions of the western blot (FIGS. 5c-d). The results from confocal microscopy imaging were consistent with those from the western blot, revealing that the mimetic TGF PA-a induced significantly more collagen II production than native rhTGF-β1 (FIG. 5c). These results indicate that the TGF PA-a nanostructures may have presented the epitopes with optimal orientation, density, and/or dynamic motion for receptor binding compared to native protein in solution. Additionally, native TGF-β1 protein has a half-life of only 2-3 min in its active form in vivo;[49] thus, the PA nanostructures may have slowed epitope degradation and improved activation kinetics relative to the native protein. Both rhTGF-β1 and TGF PA-a significantly increased aggrecan synthesis at similar levels. Cells treated with the mimetic peptide alone showed little upregulation of either protein, again indicating that the peptide alone was unable to mimic TGF-β1. Staining for F-actin also revealed that cells treated with rhTGF-β1 and TGF PA-a maintained healthy chondrocyte phenotypes and prevented hypertrophy, evidenced by regular, round or elliptical morphologies and compact cell sizes (FIGS. 5c-d). These results indicated that TGF PA-a not only enhanced ECM synthesis, but also sustained a mature chondrocyte phenotype without hypertrophy over longer periods of in vitro culture.

Three-Dimensional TGF PA Scaffolds Sustain Chondrocyte Phenotype

Figure 23:
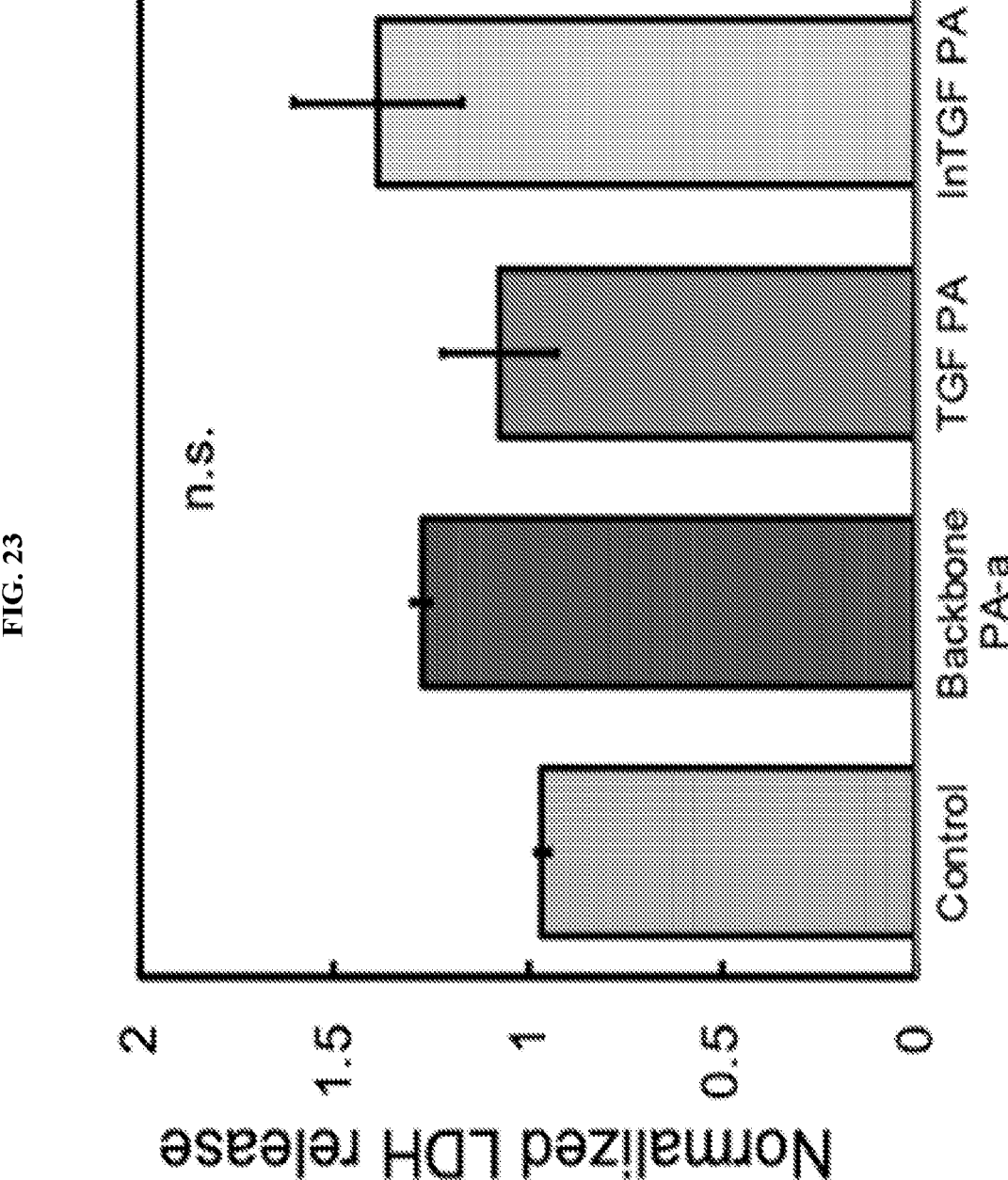
FIG. 23: LDH release from cells encapsulated in gels after three days in vitro.

Since the TGF-β1 mimetic PA nanostructures effectively activated intracellular TGF-β1 signaling and ECM synthesis, experiments were conducted during development of embodiments herein to examine their function as three-dimensional gel networks due to the important role of three-dimensional ECM organization in articular cartilage structure and function. Since TGF PA-a showed bioactivity, testing was focused on hydrogels composed of Backbone PA-a, TGF PA-a, and ln TGF PA-a. PA hydrogel networks were prepared by exposing PA solutions to calcium ions.[26] To confirm that differences in bioactivity were not caused by differences in mechanical properties of the hydrogels, scanning electron microscopy (SEM) and rheology were performed, which demonstrated that the PA hydrogels had similar morphologies and viscoelastic behavior, respectively (FIGS. 6a-d, 24, Table 2). The three PA gels had similar flow strains and moduli, indicating that they may behave similarly to shear strain in vivo. Next, chondrocytes were encapsulated inside the PA gels and cultured them for three days in vitro to measure biocompatibility and observe chondrogenic behavior. The cells withstood the encapsulation process and maintained high viability, as measured by levels of lactate dehydrogenase (LDH), a cytosolic enzyme only released upon cell lysis, in culture medium (FIG. 23). Morphology and distribution of encapsulated cells was investigated using F-actin ICC staining and confocal microscopy (FIGS. 6e-g). Since increased cell migration or clustering are indicative of osteoarthritis, dedifferentiation, and decreased chondrogenic capacity,[50-53] the phenotypic and migratory responses of chondrocytes inside the PA gels was analyzed. Although there was no significant difference in viability, the cells in each PA gel behaved significantly differently. Far fewer cells were visible within the bulk of the Backbone PA-a and ln TGF PA-a gels compared to TGF PA-a gels, despite equal concentrations of cells encapsulated (FIGS. 6e-g). In contrast, cells in TGF PA-a gels remained inside the gels and survived three days in vitro, indicating that the TGF PA-a hydrogels provided the necessary bioactive signals for a sustainable microenvironment. Furthermore, the cells displayed compact, elliptical morphologies and were well-dispersed throughout the TGF PA-a gel, resembling chondrogenic behavior in native cartilage. These cell-PA interactions indicated that, in addition to inducing chondrogenic TGF-β1 responses, our TGF-β1 mimetic PA nanostructures sustained healthy chondrocyte phenotype and behavior within a three-dimensional ECM environment.

TABLE 2

Strain and storage/loss moduli at G'/G" crossover
for Backbone PA-a only, TGF PA-a, and lnTGF PA-a.

| | G'/G" crossover % strain | G'/G" crossover storage modulus |
| --- | --- | --- |
| Backbone PA-a | 7.10 ± 1.49 | 0.55 ± 0.13 kPa |
| TGF PA-a | 5.80 ± 1.40 | 0.63 ± 1.14 kPa |
| lnTGF PA-a | 8.95 ± 1.88 | 0.17 ± 0.07 kPa |

Example 2

Slurry Formulation and In Vivo Data

Methods

PA/HA Slurry Formulation

PA solutions were prepared at 2 wt % as described for the in vitro data, and then mixed with various amounts of crosslinked hyaluronic acid particles. The resulting slurry was physically stirred and then micro-centrifuged for 15 minutes before storing at 4° C. for 24 hours to fully hydrate the HA particles. The slurry material was loaded into a 1 mL syringe with a 19-gauge needle and kept on ice until use during surgery. Fluorescently labeled PA was produced via covalent functionalization of carboxytetramethylrhodamine (TAMRA) to the C-terminus of diluent Backbone PA-a. For the fluorescently labeled PA experiments, the final co-assembly ratio was 10 mol % epitope PA, 88 mol % backbone PA, and 2 mol % TAMRA PA.

Rheology

Measurements were performed on an Anton Paar MCR302 rheometer with a 25 mm parallel-plate fixture. 120 μL of the PA/HA hybrid slurry was placed on the bottom plate and 30 μL of a 50 mM CaCl₂/75 mM NaCl gelling solution was placed on the upper fixture. The fixture was lowered to a gap of 0.5 mm for 10 min during which time a 0.1% oscillatory strain was applied with a 10 rad/s angular frequency. The gap height was allowed to vary to keep the normal force at 0 N. Next, a strain sweep was performed at 10 rad/s from 0.1% to 100% strain to measure the strain to break the gel.

Rabbit Osteochondral Defect Model

New Zealand White rabbits (2.8-3.2 kg) were used for this procedure. Prior to surgery, rabbits were clipped over the surgical site and sterilely prepped with Chlorhexidine scrub. For all rabbits, a 3 cm curvilinear incision was made over the lateral aspect of the patellar tendon. The joint capsule and synovium were incised over the lateral aspect of the joint. Following our established protocol, a circular osteochondral defect (2-3 mm diameter) approximately 3 mm deep was created in the medial condyle in each rabbit bilaterally. Approximately 30 μL of the PA/HA slurry was ejected from the syringe and packed into the defect space. After defect filling with PA/HA slurry, approximately 30 μL of a sterile 50 mM CaCl₂, 75 mM NaCl gelling solution was added dropwise on top of each defect. After lavaging the joint with saline, the synovium and joint capsule were closed in one layer using 4-0 absorbable suture in a continuous pattern. The muscle layers and subcutaneous tissue were also closed with 4-0 absorbable suture, and the skin closed with 4-0 or 5-0 absorbable suture in a subcuticular pattern. After euthanasia, operative joints were harvested and the gross appearance was documented with digital photographs. The operated medial condyles in each group then were cut using a band saw into small bone blocks, which included the defect and its associated underlying subchondral bone. The bone blocks were fixed in 10% neutral buffered formalin, and subsequently decalcified using an EDTA/Sucrose decalcifying solution (20% EDTA in 5% sucrose). After decalcification, the blocks were cut in half through the center of the defect using a razor blade and both pieces were embedded in the same block of paraffin. Successive 5 μm thick sections were prepared and stained with H&E to evaluate general morphology of the grafted site. Both stained sections (histology) and unstained sections (fluorescence) were imaged using a TissueGnostics microscope.

Results

To test the bioactivity of the TGF-mimetic PA in vivo, a solution of TGF PA-a nanofibers were mixed with cross-linked hyaluronic acid (HA) particles to produce a robust injectable slurry formulation that could be implanted into chondral defects and withstand the shear forces in the joint. Various ratios of this hybrid material were tested using a 2 wt % PA solution mixed with different amounts of HA (2-6 wt %). The storage modulus and strain required to fracture the hybrid gels increased with increasing concentration of HA (FIG. 25). In comparison to PA gels alone, the hybrid PA/HA slurries exhibited 3-4 times higher strain to break, highlighting the increased ductility and resistance to shear of the hybrid materials. While higher concentrations of HA improve the stiffness and toughness of the gels, it also results in increased volume expansion in saline which could lead to displacement of the material following implantation. Therefore, to balance mechanical toughness with minimal swelling the 2 wt % PA+4 wt % HA slurry formulation was used for in vivo studies.

To test material retention in cartilage defects in vivo, the hybrid slurry was implanted with fluorescently labeled PA into osteochondral defects in a rabbit condyle model (FIG. 26). The PA/HA slurry (pink) was clearly visible localized in the defect following implantation. Explants of the joints after 1- and 2-days post-op showed good retention of the implant in the defect as a robust clot was observed macroscopically and a clear fluorescence signal detected in the implant site. Histological staining revealed good integration of the implant with surrounding bone and cartilage tissue which is important for robust cartilage regeneration. After 7 days, the defect site showed good tissue infill macroscopically and the early stages of cartilage regeneration in histological slices. No fluorescent signal was detected from the PA material suggesting that the implant initiated the tissue regeneration process and then started to biodegrade as expected.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

REFERENCES

The following references, some of which are cited herein by number, are herein incorporated by reference in their entireties.

Vaz, E. R. et al. A Short Peptide That Mimics the Binding Domain of TGF-β1 Presents Potent Anti-Inflammatory Activity. PLoS One 10, e0136116 (2015).

Araujo, G. R. et al. TGFβ1 mimetic peptide modulates immune response to grass pollen allergens in mice. Allergy 75, 882-891 (2020).

Lourengo, T. C., Mello, L. R., Silva, B. B. S. & Silva, E. R. Molecular structure and supramolecular assembly of a TGF-β1 mimetic oligopeptide. J. Mol. Struct. 1219, 128691 (2020).

Shah, R. N. et al. Supramolecular design of self-assembling nanofibers for cartilage regeneration. Proc. Natl. Acad. Sci. U.S.A. 107, 3293-3298 (2010).

Ghatak, S. et al. Transforming growth factor 1 (TGF1)-induced CD44V6-NOX4 signaling in pathogenesis of idiopathic pulmonary fibrosis. J. Biol. Chem. 292, 10490-10519 (2017).

Li, L., Omer, B. P., Huang, T., Hinck, A. P. & Kiessling, L. L. Peptide ligands that use a novel binding site to target both TGF-β receptors. Mol. Biosyst. 6, 2392-2402 (2010). Johnston, C. J. C. et al. A structurally distinct TGF-β mimic from an intestinal helminth parasite potently induces regulatory T cells. Nat. Commun. 8, (2017).

Bhatnagar et al. Peptide compositions with growth factor-like activity. U.S. Pat. No. 5,661,127. Aug. 26, 1997.

Bhatnagar et al. Peptide compositions with growth factor-like activity. U.S. Pat. No. 5,780,436. Jul. 14, 1998.

Bhatnagar et al. Peptide compositions mimicking TGF-.beta. activity. U.S. Pat. No. 6,638,912. Oct. 28, 2003.

(1) Huey, D. J.; Hu, J. C.; Athanasiou, K. A. Unlike Bone, Cartilage Regeneration Remains Elusive. Science. American Association for the Advancement of Science Nov. 16, 2012, pp 917-921.

(2) Leifer, V. P.; Katz, J. N.; Losina, E. The Burden of OA-Health Services and Economics. Osteoarthr. Cartil. 2021.

(3) Karsdal, M. A.; Michaelis, M.; Ladel, C.; Siebuhr, A. S.; Bihlet, A. R.; Andersen, J. R.; Guehring, H.; Christiansen, C.; Bay-Jensen, A. C.; Kraus, V. B. Disease-Modifying Treatments for Osteoarthritis (DMOADs) of the Knee and Hip: Lessons Learned from Failures and Opportunities for the Future. Osteoarthr. Cartil. 2016, 24 (12), 2013-2021.

(4) Ghouri, A.; Conaghan, P. G. Update on Novel Pharmacological Therapies for Osteoarthritis. Ther. Adv. Musculoskelet. Dis. 2019, 11, 1-11.

(5) Erggelet, C.; Vavken, P. Microfracture for the Treatment of Cartilage Defects in the Knee Joint—A Golden Standard? Journal of Clinical Orthopaedics and Trauma. Elsevier B.V. Sep. 1, 2016, pp 145-152.

(6) Andriolo, L.; Reale, D.; Di Martino, A.; Boffa, A.; Zaffagnini, S.; Filardo, G. Cell-Free Scaffolds in Cartilage Knee Surgery: A Systematic Review and Meta-Analysis of Clinical Evidence. Cartilage 2019, 194760351985240.

(7) Walker, M.; Luo, J.; Pringle, E. W.; Cantini, M. ChondroGELesis: Hydrogels to Harness the Chondrogenic Potential of Stem Cells. Mater. Sci. Eng. C 2021, 121, 111822.

(8) Sophia Fox, A. J.; Bedi, A.; Rodeo, S. A. The Basic Science of Articular Cartilage: Structure, Composition, and Function. Sports Health 2009, 1 (6), 461-468.

(9) Blunk, T.; Sieminski, A. L.; Gooch, K. J.; Courter, D. L.; Hollander, A. P.; Menahem Nahir, A.; Langer, R.; Vunjak-novakovic, G.; Freed, L. E. Differential Effects of Growth Factors on Tissue-Engineered Cartilage. TISSUE Eng. 2002, 8 (1).

(10) Goldring, M. B.; Tsuchimochi, K.; Ijiri, K. The Control of Chondrogenesis. J. Cell. Biochem. 2006, 97 (1), 33-44.

(11) Wang, W.; Rigueur, D.; Lyons, K. M. TGFb Signaling in Cartilage Development and Maintenance. Birth Defects Res. (Part C) 2014, 102, 37-51.

(12) Thielen, N.; van der Kraan, P.; van Caam, A. TGFβ/BMP Signaling Pathway in Cartilage Homeostasis. Cells 2019, 8 (9), 969.

(13) Shen, J.; Li, S.; Chen, D. TGF-β Signaling and the Development of Osteoarthritis. Bone Res. 2014, 2 (14002), 1-7.

(14) Blaney Davidson, E. N.; Scharstuhl, A.; Vitters, E. L.; van der Kraan, P. M.; van den Berg, W. B. Reduced Transforming Growth Factor-Beta Signaling in Cartilage of Old Mice: Role in Impaired Repair Capacity. Arthritis Res. Ther. 2005, 7 (6), R1338.

(15) Van Beuningen, H. M.; Van der Kraan, P. M.; Arntz, O. J.; Van den Berg, W. B. Transforming Growth Factor-B1 Stimulates Articular Chondrocyte Proteoglycan Synthesis and Induces Osteophyte Formation in the Murine Knee Joint. Lab. Investig. 1994, 71 (2), 279-290.

(16) Wang, W.; Li, B.; Yang, J.; Xin, L.; Li, Y.; Yin, H.; Qi, Y.; Jiang, Y.; Ouyang, H.; Gao, C. The Restoration of Full-Thickness Cartilage Defects with BMSCs and TGF-Beta 1 Loaded PLGA/Fibrin Gel Constructs. Biomaterials 2010, 31 (34), 8964-8973.

(17) Reyes, R.; Delgado, A.; Sánchez, E.; Fernandez, A.; Hernandez, A.; Evora, C. Repair of an Osteochondral Defect by Sustained Delivery of BMP-2 or TGFβ1 from a Bilayered Alginate-PLGA Scaffold. J. Tissue Eng. Regen. Med. 2012, 8 (7), n/a-n/a.

(18) Lewis, J. A.; Freeman, R.; Carrow, J. K.; Clemons, T. D.; Palmer, L. C.; Stupp, S. I. Transforming Growth Factor 0-1 Binding by Peptide Amphiphile Hydrogels. ACS Biomater. Sci. Eng. 2020, 6 (8), acsbiomaterials.0c00679.

(19) Shah, R. N.; Shah, N. A.; Lim, M. M. D. R.; Hsieh, C.; Nuber, G.; Stupp, S. I. Supramolecular Design of Self-Assembling Nanofibers for Cartilage Regeneration. Proc. Natl. Acad. Sci. U.S.A. 2010, 107 (8), 3293-3298.

(20) Massagué, J. TGFβ Signalling in Context. Nat. Rev. Mol. Cell Biol. 2012, 13 (10), 616-630.

(21) Vaz, E. R.; Fujimura, P. T.; Araujo, G. R.; da Silva, C. A. T.; Silva, R. L.; Cunha, T. M.; Lopes-Ferreira, M.; Lima, C.; Ferreira, M. J.; Cunha-Junior, J. P.; Taketomi, E. A.; Goulart, L. R.; Ueira-Vieira, C. A Short Peptide That Mimics the Binding Domain of TGF-B1 Presents Potent Anti-Inflammatory Activity. PLoS One 2015, 10 (8), e0136116.

(22) Araujo, G. R.; Aglas, L.; Vaz, E. R.; Machado, Y.; Huber, S.; Himly, M.; Duschl, A.; Goulart, L. R.; Ferreira, F. TGFβ1 Mimetic Peptide Modulates Immune Response to Grass Pollen Allergens in Mice. Allergy 2020, 75 (4), 882-891.

(23) Lourengo, T. C.; Mello, L. R.; Silva, B. B. S.; Silva, E. R. Molecular Structure and Supramolecular Assembly of a TGF-B1 Mimetic Oligopeptide. J. Mol. Struct. 2020, 1219, 128691.

(24) Liu, Q.; Jia, Z.; Duan, L.; Xiong, J.; Wang, D.; Ding, Y. Functional Peptides for Cartilage Repair and Regeneration. Am. J. Transl. Res. 2018, 10 (2), 501-510.

(25) Gresham, R. C. H.; Bahney, C. S.; Leach, J. K. Growth Factor Delivery Using Extracellular Matrix-Mimicking Substrates for Musculoskeletal Tissue Engineering and Repair. Bioact. Mater. 2021, 6 (7), 1945-1956.

(26) Hartgerink, J. D.; Beniash, E.; Stupp, S. I. Self-Assembly and Mineralization of Peptide-Amphiphile Nanofibers. Science. 2001, 294 (5547), 1684-1688.

(27) Hendricks, M. P.; Sato, K.; Palmer, L. C.; Stupp, S. I. Supramolecular Assembly of Peptide Amphiphiles. *Acc. Chem. Res.* 2017, 50 (10), 2440-2448.

(28) Silva, G. A.; Czeisler, C.; Niece, K. L.; Beniash, E.; Harrington, D. A.; Kessler, J. A.; Stupp, S. I. Selective Differentiation of Neural Progenitor Cells by High-Epitope Density Nanofibers. *Science.* 2004, 303 (5662), 1352-1355.

(29) Beniash, E.; Hartgerink, J. D.; Storrie, H.; Stendahl, J. C.; Stupp, S. I. Self-Assembling Peptide Amphiphile Nanofiber Matrices for Cell Entrapment. *Acta Biomater.* 2005, 1 (4), 387-397.

(30) Berns, E. J.; Álvarez, Z.; Goldberger, J. E.; Boekhoven, J.; Kessler, J. A.; Kuhn, H. G.; Stupp, S. I. A Tenascin-C Mimetic Peptide Amphiphile Nanofiber Gel Promotes Neurite Outgrowth and Cell Migration of Neurosphere-Derived Cells. *Acta Biomater.* 2016, 37, 50-58.

(31) Edelbrock, A. N.; Àlvarez, Z.; Simkin, D.; Fyrner, T.; Chin, S. M.; Sato, K.; Kiskinis, E.; Stupp, S. I. Supramolecular Nanostructure Activates TrkB Receptor Signaling of Neuronal Cells by Mimicking Brain-Derived Neurotrophic *Factor. Nano Lett.* 2018, 18 (10), 6237-6247.

(32) Sur, S.; Tantakitti, F.; Matson, J. B.; Stupp, S. I. Epitope Topography Controls Bioactivity in Supramolecular Nanofibers. *Biomater. Sci.* 2015, 3 (3), 520-532.

(33) Da Silva, R. M. P.; Van Der Zwaag, D.; Albertazzi, L.; Lee, S. S.; Meijer, E. W.; Stupp, S. I. Super-Resolution Microscopy Reveals Structural Diversity in Molecular Exchange among Peptide Amphiphile Nanofibres. *Nat. Commun.* 2016, 7 (1), 1-10.

(34) Dems, D.; Freeman, R.; Riker, K. D.; Coradin, T.; Stupp, S. I.; Aimé, C. Multivalent Clustering of Adhesion Ligands in Nanofiber-Nanoparticle Composites. *Acta Biomater.* 2021, 119, 303-311.

(35) Newcomb, C. J.; Sur, S.; Ortony, J. H.; Lee, O. S.; Matson, J. B.; Boekhoven, J.; Yu, J. M.; Schatz, G. C.; Stupp, S. I. Cell Death versus Cell Survival Instructed by Supramolecular Cohesion of Nanostructures. *Nat. Commun.* 2014, 5 (1), 1-10.

(36) Álvarez, Z.; Kolberg-Edelbrock, A. N.; Sasselli, I. R.; Ortega, J. A.; Qiu, R.; Syrgiannis, Z.; Mirau, P. A.; Chen, F.; Chin, S. M.; Weigand, S.; Kiskinis, E.; Stupp, S. I. Bioactive Scaffolds with Enhanced Supramolecular Motion Promote Recovery from Spinal Cord Injury. *Science.* 2021, 374 (6569), 848-856.

(37) Yuan, S. C.; Lewis, J. A.; Sai, H.; Weigand, S. J.; Palmer, L. C.; Stupp, S. I. Peptide Sequence and Self-Assembly Pathway Direct Supramolecular Morphology and Cell-Material Interactions. *Prep.*

(38) Tantakitti, F.; Boekhoven, J.; Wang, X.; Kazantsev, R. V.; Yu, T.; Li, J.; Zhuang, E.; Zandi, R.; Ortony, J. H.; Newcomb, C. J.; Palmer, L. C.; Shekhawat, G. S.; De La Cruz, M. O.; Schatz, G. C.; Stupp, S. I. Energy Landscapes and Functions of Supramolecular Systems. *Nat. Mater.* 2016, 15 (4), 469-476.

(39) Sato, K.; Ji, W.; Palmer, L. C.; Weber, B.; Barz, M.; Stupp, S. I. Programmable Assembly of Peptide Amphiphile via Noncovalent-to-Covalent Bond Conversion. *J. Am. Chem. Soc.* 2017, 139 (26), 8995-9000.

(40) Li, T.; Senesi, A. J.; Lee, B. Small Angle X-Ray Scattering for Nanoparticle Research. *Chemical Reviews.* American Chemical Society Sep. 28, 2016, pp 11128-11180.

(41) Greenfield, N.; Fasman, G. D. Computed Circular Dichroism Spectra for the Evaluation of Protein Conformation. *Biochemistry* 1967, 8 (10), 4108-4116.

(42) Jackson, M.; Mantsch, H. H. The Use and Misuse of FTIR Spectroscopy in the Determination of Protein Structure. *Crit. Rev. Biochem. Mol. Biol.* 1995, 30 (2), 95-120.

(43) Gosal, W. S.; Morten, I. J.; Hewitt, E. W.; Smith, D. A.; Thomson, N. H.; Radford, S. E. Competing Pathways Determine Fibril Morphology in the Self-Assembly of b 2-Microglobulin into Amyloid. *J. Mol. Biol.* 2005, 351 (4), 850-864.

(44) Dasch, J. R.; Pace, D. R.; Waegell, W.; Inenaga, D.; Ellingsworth, L. Monoclonal Antibodies Recognizing Transforming Growth Factor-Beta. Bioactivity Neutralization and Transforming Growth Factor Beta 2 Affinity Purification. *J. Immunol.* 1989, 142 (5).

(45) Xie, L.; Tintani, F.; Wang, X.; Li, F.; Zhen, G.; Qiu, T.; Wan, M.; Crane, J.; Chen, Q.; Cao, X. Systemic Neutralization of TGF-β Attenuates Osteoarthritis. *Ann. N. Y. Acad. Sci.* 2016, 1376 (1), 53-64.

(46) Teicher, B. A. TGFβ-Directed Therapeutics: 2020. *Pharmacol. Ther.* 2021, 217, 107666.

(47) Loeser, R. F. Integrins and Chondrocyte-Matrix Interactions in Articular Cartilage. *Matrix Biol.* 2014, 39, 11-16.

(48) Wipff, P. J.; Hinz, B. Integrins and the Activation of Latent Transforming Growth Factor B1—An Intimate Relationship. *Eur. J. Cell Biol.* 2008, 87 (8-9), 601-615.

(49) Wakefield, L. M.; Winokur, T. S.; Hollands, R. S.; Christopherson, K.; Levinson, A. D.; Sporn, M. B. Recombinant Latent Transforming Growth Factor Beta 1 Has a Longer Plasma Half-Life in Rats than Active Transforming Growth Factor Beta 1, and a Different Tissue Distribution. *J. Clin. Invest.* 1990, 86 (6), 1976-1984.

(50) Koelling, S.; Kruegel, J.; Irmer, M.; Path, J. R.; Sadowski, B.; Miro, X.; Miosge, N. Migratory Chondrogenic Progenitor Cells from Repair Tissue during the Later Stages of Human Osteoarthritis. *Cell Stem Cell* 2009, 4 (4), 324-335.

(51) O'Connell, G. D.; Tan, A. R.; Cui, V.; Bulinski, J. C.; Cook, J. L.; Attur, M.; Abramson, S. B.; Ateshian, G. A.; Hung, C. T. Human Chondrocyte Migration Behaviour to Guide the Development of Engineered Cartilage. *J. Tissue Eng. Regen. Med.* 2017, 11 (3), 877-886.

(52) Wang, Y.-X.; Zhao, Z.-D.; Wang, Q.; Li, Z.-L.; Huang, Y.; Zhao, S.; Hu, W.; Liang, J.-W.; Li, P.-L.; Wang, H.; Mao, N.; Wu, C.-T.; Zhu, H. Biological Potential Alterations of Migratory Chondrogenic Progenitor Cells during Knee Osteoarthritic Progression. *Arthritis Res. Ther.* 2020, 22, 1-13.

(53) Hall, A. C. The Role of Chondrocyte Morphology and Volume in Controlling Phenotype—Implications for Osteoarthritis, Cartilage Repair, and Cartilage Engineering. *Current Rheumatology Reports.* Current Medicine Group LLC 1 Aug. 1, 2019.

SEQUENCE LISTING

Sequence total quantity: 13
SEQ ID NO: 1          moltype = AA   length = 9
FEATURE               Location/Qualifiers -continued

```
source                1..9
                      mol_type = protein
                      organism = unidentified
SEQUENCE: 1
CESPLKRQC                                                          9

SEQ ID NO: 2          moltype = AA   length = 9
FEATURE               Location/Qualifiers
source                1..9
                      mol_type = protein
                      organism = synthetic construct
SEQUENCE: 2
SESPLKRQS                                                          9

SEQ ID NO: 3          moltype = AA   length = 6
FEATURE               Location/Qualifiers
source                1..6
                      mol_type = protein
                      organism = synthetic construct
SEQUENCE: 3
VVVAAA                                                             6

SEQ ID NO: 4          moltype = AA   length = 6
FEATURE               Location/Qualifiers
source                1..6
                      mol_type = protein
                      organism = synthetic construct
SEQUENCE: 4
AAAVVV                                                             6

SEQ ID NO: 5          moltype = AA   length = 4
FEATURE               Location/Qualifiers
source                1..4
                      mol_type = protein
                      organism = synthetic construct
SEQUENCE: 5
AAVV                                                               4

SEQ ID NO: 6          moltype = AA   length = 4
FEATURE               Location/Qualifiers
source                1..4
                      mol_type = protein
                      organism = synthetic construct
SEQUENCE: 6
VVAA                                                               4

SEQ ID NO: 7          moltype = AA   length = 4
FEATURE               Location/Qualifiers
source                1..4
                      mol_type = protein
                      organism = synthetic construct
SEQUENCE: 7
AAEE                                                               4

SEQ ID NO: 8          moltype = AA   length = 4
FEATURE               Location/Qualifiers
source                1..4
                      mol_type = protein
                      organism = synthetic construct
SEQUENCE: 8
AEAE                                                               4

SEQ ID NO: 9          moltype = AA   length = 9
FEATURE               Location/Qualifiers
source                1..9
                      mol_type = protein
                      organism = synthetic construct
SEQUENCE: 9
VVVAAAEEE                                                          9

SEQ ID NO: 10         moltype = AA   length = 9
FEATURE               Location/Qualifiers
source                1..9
                      mol_type = protein
                      organism = synthetic construct
SEQUENCE: 10
EEEAAAVVV                                                          9

SEQ ID NO: 11         moltype = AA   length = 4
```

-continued

```
FEATURE              Location/Qualifiers
source               1..4
                     mol_type = protein
                     organism = synthetic construct
SEQUENCE: 11
EEAA                                                            4

SEQ ID NO: 12        moltype = AA  length = 9
FEATURE              Location/Qualifiers
source               1..9
                     mol_type = protein
                     organism = synthetic construct
SEQUENCE: 12
VVVAAAKKK                                                       9

SEQ ID NO: 13        moltype = AA  length = 9
FEATURE              Location/Qualifiers
source               1..9
                     mol_type = protein
                     organism = synthetic construct
SEQUENCE: 13
VVVAAAEEE                                                       9
```

The invention claimed is:

1. A composition comprising a bioactive peptide amphiphile (PA) comprising:

(i) a hydrophobic non-peptidic segment;

(ii) a β-sheet-forming peptide segment;

(iii) an acidic peptide segment; and (iv) a TGF-β1 mimetic epitope peptide, wherein the TGF-β1 mimetic epitope peptide consists of CESPLKRQC (SEQ ID NO: 1), and wherein the TGF-β1 mimetic epitope peptide is cyclized via disulfide bonds between the terminal cysteine residues.

2. The composition of claim 1, wherein the hydrophobic non-peptidic segment of the bioactive peptide amphiphile comprises an acyl chain.

3. The composition of claim 2, wherein the acyl chain comprises $C_6$-$C_{20}$.

4. The composition of claim 1, wherein the β-sheet-forming peptide segment of the bioactive peptide amphiphile comprises a combination of 2-6 V and/or A residues and/or wherein the acidic peptide segment of the bioactive peptide amphiphile comprises a combination of 1-4 Glu (E) and/or Asp (D) residues.

5. The composition of claim 4, wherein the β-sheet-forming peptide segment of the bioactive peptide amphiphile is selected from the group consisting of VVVAAA (SEQ ID NO: 3), AAAVVV (SEQ ID NO: 4), AAVV (SEQ ID NO: 5), VVAA (SEQ ID NO: 6), AA, VV, VA, and AV.

6. The composition of claim 4, wherein the acidic peptide segment is selected from the group consisting of E, EE, EEE, D, DD, DDD, ED, DE, EDE, DED, EDD, and DEE.

7. The composition of claim 1, comprising a backbone PA of the bioactive peptide amphiphile selected from the group consisting of $C_{16}$-AAEE (SEQ ID NO: 7), $C_{16}$-AEAE (SEQ ID NO: 8), and $C_{16}$-VVVAAAEEE (SEQ ID NO: 9).

8. The composition of claim 7, wherein the TGF-β1 mimetic epitope peptide is tethered to the backbone PA by a lysine linker.

9. The composition of claim 1, further comprising diluent PA comprising:

(i) a hydrophobic non-peptidic segment;

(ii) a β-sheet-forming peptide segment; and (iii) a charged peptide segment.

10. The composition of claim 9, wherein the hydrophobic non-peptidic segment of the diluent peptide amphiphile comprises an acyl chain comprising $C_6$-$C_{20}$.

11. The composition of claim 9, wherein the β-sheet-forming peptide segment of the diluent peptide amphiphile comprises a combination of 2-6 V and/or A residues and/or wherein the charged peptide segment of the diluent peptide amphiphile comprises a combination of 1-4 Glu (E) and/or Asp (D) residues.

12. The composition of claim 11, wherein the β-sheet-forming peptide segment of the diluent peptide amphiphile is selected from the group consisting of VVVAAA (SEQ ID NO: 3), AAAVVV (SEQ ID NO: 4), AAVV (SEQ ID NO: 5), VVAA (SEQ ID NO: 6), AA, VV, VA, and AV.

13. The composition of claim 11, wherein the charged peptide segment of the diluent peptide amphiphile is selected from the group consisting of E, EE, EEE, D, DD, DDD, ED, DE, EDE, DED, EDD, and DEE.

14. The composition of claim 9, comprising a backbone PA of the diluent peptide amphiphile selected from the group consisting of $C_{16}$-AAEE (SEQ ID NO: 7), $C_{16}$-AEAE (SEQ ID NO: 8), and $C_{16}$-VVVAAAEEE (SEQ ID NO: 9).

15. The composition of claim 9, comprising 5%-95% (by mol) of the bioactive peptide amphiphile and 5%-95% (by mol) of the diluent peptide amphiphile.

16. The composition of claim 9, wherein the bioactive PA and the diluent PA co-assemble into a helical ribbon-like structure having an average diameter of 50 to 60 nm.

17. A composite material comprising a composition of claim 1 and a biocompatible polymer.

18. A method of promoting cartilage repair or regeneration, treating osteoarthritis or a musculoskeletal disease or injury, or preventing osteoarthritis or a musculoskeletal disease or injury, comprising administering the composition of claim 1 to a subject, wherein the subject is suffering from a cartilage defect or injury or is at elevated risk for osteoarthritis or a musculoskeletal disease or injury.

* * * * *